United States Patent
Graham et al.

(10) Patent No.: US 7,141,532 B2
(45) Date of Patent: Nov. 28, 2006

(54) PROCESS FOR THE PREPARATION OF A DRY PESTICIDAL COMPOSITION CONTAINING A DICARBOXYLATE COMPONENT

(75) Inventors: Jeffrey A. Graham, Chesterfield, MO (US); William Abraham, Wildwood, MO (US); John T. Wang, St. Louis, MO (US); Beth J. Calabotta, University City, MO (US); Brent D. Massmann, Ballwin, MO (US); William H. Miller, Glendale, MO (US)

(73) Assignee: Monsanto Technology LLC, St. Louis, MO (US)

( * ) Notice: Subject to any disclaimer, the term of this patent is extended or adjusted under 35 U.S.C. 154(b) by 415 days.

(21) Appl. No.: 10/653,332

(22) Filed: Sep. 2, 2003

(65) Prior Publication Data
US 2004/0077499 A1    Apr. 22, 2004

Related U.S. Application Data

(60) Provisional application No. 60/407,479, filed on Aug. 31, 2002.

(51) Int. Cl.
| | | |
|---|---|---|
| *A01N 25/12* | (2006.01) | |
| *A01N 25/30* | (2006.01) | |
| *A01N 57/02* | (2006.01) | |
| *A01P 13/00* | (2006.01) | |
| *B01F 17/00* | (2006.01) | |

(52) U.S. Cl. .................. 504/206; 504/367; 516/109
(58) Field of Classification Search ............... 504/206, 504/367; 516/109
See application file for complete search history.

(56) References Cited

U.S. PATENT DOCUMENTS 3,671,612 A     6/1972 Roszinski et al.

(Continued)

FOREIGN PATENT DOCUMENTS

EP     0 238 240 A2     9/1987

(Continued)

OTHER PUBLICATIONS

Turner, D. J. "Effects on glyphosate performance of formulation, additives and mixing with other herbicides". Chapter 15 of The Herbicide Glyphosate. Grossbard et al, ed. p. 229-230. 1985.*

(Continued)

*Primary Examiner*—S. Mark Clardy
(74) *Attorney, Agent, or Firm*—Senniger Powers; Joseph A. Schaper

(57) ABSTRACT

A process for preparing a dry pesticidal composition including a glyphosate component comprising a water-soluble salt of glyphosate acid, a dicarboxylate component and optionally an adjuvant component. According to the process of the present invention, a glyphosate component is combined with a dicarboxylate component and optionally an adjuvant component to form an enhanced pesticidal composition. The glyphosate component and/or the dicarboxylate component may be combined in their salt form or either or both may be combined in acid form and reacted in the mixture with a base component to form the corresponding salt.

99 Claims, 9 Drawing Sheets

U.S. PATENT DOCUMENTS

| | | |
|---|---|---|
| 3,799,758 A | 3/1974 | Franz |
| 4,140,513 A | 2/1979 | Prill |
| 4,159,901 A | 7/1979 | Beestman et al. |
| 4,315,765 A | 2/1982 | Large |
| 4,397,676 A | 8/1983 | Bakel |
| 4,405,531 A | 9/1983 | Franz |
| 4,481,026 A | 11/1984 | Prisbylla |
| 4,507,250 A | 3/1985 | Bakel |
| 4,840,659 A | 6/1989 | Franz |
| 5,047,079 A | 9/1991 | Djafar et al. |
| 5,070,197 A | 12/1991 | Chin et al. |
| 5,266,553 A | 11/1993 | Champion et al. |
| 5,324,708 A | 6/1994 | Moreno et al. |
| 5,389,598 A | 2/1995 | Berk et al. |
| 5,410,075 A | 4/1995 | Moreno et al. |
| 5,430,005 A | 7/1995 | Kassebaum et al. |
| 5,436,220 A | 7/1995 | Hickey |
| 5,525,576 A | 6/1996 | Medina-Vega et al. |
| 5,563,111 A | 10/1996 | Hioki et al. |
| 5,612,285 A | 3/1997 | Arnold |
| 5,614,468 A | 3/1997 | Kramer et al. |
| 5,622,911 A | 4/1997 | Hasebe et al. |
| 5,633,397 A | 5/1997 | Gillespie et al. |
| 5,656,572 A | 8/1997 | Kuchikata et al. |
| 5,693,593 A | 12/1997 | Arnold |
| 5,703,015 A | 12/1997 | Berger et al. |
| 5,716,903 A | 2/1998 | Kramer et al. |
| 5,750,468 A | 5/1998 | Wright et al. |
| 5,795,847 A | 8/1998 | Nielsen et al. |
| 5,849,663 A | 12/1998 | Hasebe et al. |
| 5,863,863 A | 1/1999 | Hasebe et al. |
| 5,863,909 A | 1/1999 | Kurita et al. |
| 5,948,421 A | 9/1999 | Okano et al. |
| 5,985,794 A | 11/1999 | Hasebe et al. |
| 5,985,798 A | 11/1999 | Crudden |
| 5,998,332 A | 12/1999 | Sato et al. |
| 6,008,158 A | 12/1999 | Hasebe et al. |
| 6,030,923 A | 2/2000 | Okano et al. |
| 6,051,533 A | 4/2000 | Kajikawa et al. |
| 6,063,733 A | 5/2000 | Berger et al. |
| 6,093,679 A | 7/2000 | Azuma et al. |
| 6,117,820 A | 9/2000 | Cutler et al. |
| 6,180,566 B1 | 1/2001 | Nielsen et al. |
| 6,218,336 B1 | 4/2001 | Coleman |
| 6,245,713 B1 | 6/2001 | Brinker et al. |
| 6,313,074 B1 | 11/2001 | Suzuki et al. |
| 6,448,434 B1 | 9/2002 | Kramer |
| 6,475,954 B1 | 11/2002 | Hamroll et al. |
| 6,599,858 B1 | 7/2003 | Kramer |
| 6,605,568 B1 * | 8/2003 | Massmann et al. ......... 504/127 |
| 2002/0049140 A1 | 4/2002 | Hamroll et al. |

FOREIGN PATENT DOCUMENTS

| | | |
|---|---|---|
| EP | 0 378 985 A1 | 7/1990 |
| EP | 0 394 211 A1 | 10/1990 |
| EP | 0 256 608 B1 | 4/1992 |
| EP | 0 582 561 A1 | 2/1994 |
| EP | 1 203 532 A1 | 5/2002 |
| FR | 2 692 439 A1 | 12/1993 |
| WO | WO 87/04595 | 8/1987 |
| WO | WO 90/07275 | 7/1990 |
| WO | WO 92/12637 | 8/1992 |
| WO | WO 92/18513 | 10/1992 |
| WO | WO 94/10844 | 5/1994 |
| WO | WO 95/17817 | 7/1995 |
| WO | WO 96/40696 | 12/1996 |
| WO | WO 96/40697 | 12/1996 |
| WO | WO 01/08480 A1 | 2/2001 |
| WO | WO 01/08492 A1 | 2/2001 |
| WO | WO 01/30157 A1 | 5/2001 |
| WO | WO 01/89302 A2 | 11/2001 |
| WO | WO 02/069718 A2 | 9/2002 |

OTHER PUBLICATIONS

International Search Report for Application No. PCT/US 03/27229, dated Feb. 24, 2004, 5 pages.

International Search Report for Application No. PCT/US 03/27195, dated Feb. 9, 2004, 11 pages.

"Herbicidal compositions containing N-phosphonomethyl glycines" Research Disclosure, Kenneth Mason Publications, Hampshire, GB, No. 15334, 1977, p. 35-36, XP002018087 ISSN: 0374-4353.

International Search Report for Application No. PCT/US 00/20337, dated Nov. 15, 2000, 3 pages.

Research Disclosure Publication No. RD 15334, Industrial Opportunities Ltd., Jan. 1977, Homewell-Havant-Hampshire P09 1EF, United Kingdom.

Turner, D.J. et al., "Complexing agents as herbicide additives", *Weed Research*, 1978, pp. 199-207, vol. 18, Blackwell Scientific Publications.

Turner, D.J., "Polybasic acids and their salts and esters," The Herbicide Glyphosate, 1985, pp. 229-230, Chapter 15, Butterworths.

Turner, D.J., "Effects on Glyphosate Performance of Formulation, Additives and Mixing with other Herbicides," The Herbicide Glyphosate, 1985, pp. 221-240.

* cited by examiner

PROCESS FOR THE PREPARATION OF A DRY PESTICIDAL COMPOSITION CONTAINING A DICARBOXYLATE COMPONENT

CROSS-REFERENCE TO RELATED APPLICATIONS

This application claims the benefit of U.S. provisional application Ser. No. 60/407,479, filed Aug. 31, 2002, the entire disclosure of which is incorporated herein by reference.

FIELD OF THE INVENTION

The present invention relates to preparation of a dry pesticidal composition useful in agriculture and in other situations where control of weeds or other vegetation is desired. In particular, it relates to a process for preparing a dry pesticidal composition including a glyphosate component comprising a water-soluble salt of glyphosate, a dicarboxylate component and optionally an adjuvant component. According to the process of the present invention, a glyphosate component is combined with a dicarboxylate component and optionally an adjuvant component to form an enhanced pesticidal solid mixture. The glyphosate component and/or the dicarboxylate component may be combined in their salt form or either or both may be combined in acid form and reacted in the mixture with a base component to form the corresponding salt.

BACKGROUND OF THE INVENTION

N-phosphonomethylglycine [$PO(OH)_2CH_2NHCH_2COOH$], which is commonly referred to as glyphosate acid or simply glyphosate, is well known in the art as a highly effective herbicide. It is also known that glyphosate, an organic acid, has relatively low solubility in water. Thus, glyphosate is typically formulated as a water-soluble salt, particularly as the mono-isopropylamine (IPA) salt, to kill or control weeds or plants. Glyphosate salt is sold commercially as an aqueous concentrate or dry salt by Monsanto Company of St. Louis, Mo. (U.S.A.) under the registered trademark ROUNDUP.

Various salts of glyphosate, methods for preparing salts of glyphosate, formulations of glyphosate and methods of use for killing and controlling weeds and plants are disclosed in U.S. Pat. Nos. 3,799,758 and 4,405,531 issued to John E. Franz. Other U.S. Patents which disclose salts of glyphosate include U.S. Pat. No. 4,315,765 issued to George B. Large, U.S. Pat. Nos. 4,507,250 and 4,397,676 issued to Izak Bakel, U.S. Pat. No. 4,481,026 issued to Michael P. Prisbylla and U.S. Pat. No. 4,140,513 issued to Erhard J. Prill. All of the foregoing patents, in their entireties, are incorporated herein by reference.

ROUNDUP brand herbicide is sold as a water-soluble liquid concentrate. However, efforts have recently been made in the art to develop water-soluble dry/solid glyphosate formulations which have the equivalent efficacy of ROUNDUP. Conventional reasons underlying these efforts have been desired cost savings in connection with the packaging, shipment and storage of a solid formulation versus a liquid. As can be appreciated, aqueous concentrates include a significant amount of water that adds to the size and weight of packaging containers and increases costs associated with post-manufacture delivery of the product to market. Less readily apparent benefits of making a dry, water-soluble glyphosate formulation, such as a granular formulation, include superior handling characteristics (e.g., controlled spillage) and the expectation that such formulations will be substantially lighter and less awkward to transport (and often hand carry) thereby making the product better suited for use in remote geographic locations.

Making a dry glyphosate formulation, however, entails overcoming inherent disadvantages relating principally to the increased production cost and comparative complexity of compounding a solid product from a combination of liquid and solid components rather than making a product in solution from the same components.

Several methods for making a solid, water-soluble, glyphosate salt-containing composition are known. For example, U.S. Pat. No. 5,047,079 issued to Djafar discloses a method for preparing a phytotoxic composition comprising admixing highly hygroscopic isopropylamine salt of glyphosate acid with a molten surfactant to form a matrix, the surfactant being a solid at ambient temperatures.

U.S. Pat. No. 5,070,197 issued to Chin, et. al. discloses an extrusion method in which a Bronsted acid, N-phosphonomethylglycine for example, is intimately admixed with a base, sodium hydroxide for example, in an extruder to produce a granular extrudate having a residual moisture content of no greater than 10%. Another method involving the production of a dry sodium glyphosate composition, albeit not involving extrusion, is disclosed in PCT application Publication No. WO 87/04595.

U.S. Pat. No. 5,266,553 issued to Champion, et al. discloses a process for preparing a dry water-soluble salt of a herbicide having a carboxylic acid functionality wherein a solution or slurry of the salt is prepared by reacting the herbicide in acid form with a sufficient amount of a neutralizing base in the presence of water to neutralize the herbicide by about 98 to about 100 mole percent and the solution or slurry is then dried. The process is primarily directed to ammonium and alkylammonium salts of substituted benzoic acid and phenoxy-substituted carboxylic acid herbicides, but the process is said to be useful also for salts of glyphosate.

In French Patent Publication No. 2.692.439 assigned to Productos Osa SACIFIA, there is generally described a phytotoxic preparation comprising the mono-ammonium salt of N-phosphonomethylglycine as a powder or granule in combination with a wetting agent, surfactant and/or a pulverulent additive. As exemplified in the reference, the mono-ammonium salt is derived from reacting glyphosate acid with ammonium bicarbonate.

U.S. Pat. No. 5,324,708 issued to Moreno, et. al. discloses a composition and related methods for preparing and using a non-hygroscopic mono-ammonium glyphosate salt such as the mono-isopropylammonium salt of N-phosphonomethylglycine and the mono-isopropylammonium salt of (3-amino-3-carboxypropyl)-methane phosphonic acid in dry powder form.

PCT application Publication No. WO 94/10844 discloses a dry glyphosate composition in which N-phosphonomethylglycine is admixed with, inter alia, an inorganic or organic, non-caustic base material such as di-ammonium phosphate or a basic guanidine salt such as guanidinium acetate.

EPO application Publication No. 0 394 211 discloses an invention comprising a dry pesticidal composition and related methods for use and production. More particularly, the invention relates to the enhanced solubility of the pesticidal composition as achieved by the addition of an effective amount of an organosilicone block copolymer or a fluorocarbon wetting agent.

PCT application Publication No. WO 90/07275 discloses an invention by which granular, water-soluble glyphosate compositions are made as by admixing, pan granulation, drying, spraying and extrusion.

PCT application Publication No. WO 92/12637 discloses water-soluble tablets containing glyphosate acid, an acid acceptor such as sodium oxalate, and an optional anionic surfactant. The acid acceptor is said to solubilize glyphosate acid through glyphosate salt formation upon exposure to water.

PCT application Publication No. WO 01/08492 discloses, a process for preparing a dry granular herbicidal composition, comprising forming an ammonium glyphosate paste by mixing in a suitable vessel particulate glyphosate acid, ammonia in an amount of about 0.8 to about 1.25 moles per mole of the glyphosate acid, and water in an amount of about 10% to about 25% by weight of all materials being mixed in the vessel, thereby causing a reaction of the glyphosate acid and ammonia that generates heat causing partial evaporation of the water, and forms the ammonium glyphosate paste having a moisture content of about 5% to about 20% by weight. If the moisture content of the paste is greater than about 15% by weight, heat and/or vacuum is applied to reduce the moisture content to about 5% to about 15% by weight. Thereafter, one or more surfactants are added to the paste, with mixing, in a weight ratio of total surfactant to ammonium glyphosate of about 1:9 to about 1:3 to form an extrudable wet mix. The wet mix is extruded to form extrudate strands that break to form moist coherent granules that are dried to produce the dry granular composition.

U.S. Pat. No. 6,599,858 issued to Kramer discloses, a process for preparing ammonium glyphosate flakes, comprising mixing solid particulate glyphosate acid, water in an amount of about 0.5 to about 3 parts by weight of glyphosate acid and a base that supplies ammonium cations to form an aqueous reaction medium. The glyphosate acid reacts with the base to form a concentrated aqueous solution of which is further processed to form dry flakes of ammonium glyphosate.

U.S. Pat. No. 6,448,434 issued to Kramer discloses, a process for preparing ammonium glyphosate flakes, comprising mixing solid particulate glyphosate acid, water in an amount of about 0.5 to about 3 parts by weight of glyphosate acid and a base that supplies ammonium cations to form an aqueous reaction medium. The glyphosate acid reacts with the base to form a concentrated aqueous solution of which is then dried to form a particulate solid ammonium glyphosate. The particulate solid ammonium glyphosate is jet milled to form a powder ammonium glyphosate.

SUMMARY OF THE INVENTION

Among the objects of the present invention are the provision of a process for the preparation of a water-soluble pesticidal composition comprising a water-soluble salt of glyphosate acid and a dicarboxylate component and optionally an adjuvant component; the provision of such a process in which particulate glyphosate acid and/or the dicarboxylate component comprising a dicarboxylic acid is reacted with a base component to form a reaction mass comprising a water-soluble salt of glyphosate and/or the salt of the dicarboxylic acid; the provision of such a process wherein the heat of reaction generated by the reaction between particulate glyphosate acid and the base component is used to cause partial evaporation of the water from of the reaction mass; the provision of such a process wherein the moisture content of the reaction mass is reduced to form a paste comprising a water-soluble salt of glyphosate acid and a dicarboxylate component; the provision of such a process wherein the paste is suitable for downstream processing to form a dry granular pesticidal composition; the provision of such a process wherein the adjuvant component is added to the reaction mass to improve the rate of formation of the water-soluble salt of glyphosate acid and/or reduce the flow resistance of the reaction mass; the provision of such a process wherein an additional quantity of adjuvant component is subsequently added to form an extrudable paste mixture; and the provision of such a process wherein the process is conducted continuously.

Briefly, therefore, the present invention is directed to a process for preparing a water-soluble pesticidal composition comprising a water-soluble salt of glyphosate acid and a dicarboxylate component. In one embodiment, the process comprises adding to a reactor a glyphosate component comprising particulate glyphosate acid, a base component, water and optionally an adjuvant component thereby causing a reaction of glyphosate acid and the base component to form a reaction mass comprising the water-soluble salt of glyphosate acid. A dicarboxylate component is also added to the reactor.

In another embodiment, the process for preparing a water-soluble pesticidal composition comprising a water-soluble salt of glyphosate acid and a dicarboxylate component comprises adding a glyphosate component comprising particulate glyphosate acid, a base component, water and optionally an adjuvant component to a reactor. The glyphosate acid and base component are thereby caused to react to form a reaction mass comprising the water-soluble salt of glyphosate acid. The moisture content of the reaction mass is reduced using the heat generated by the reaction between the particulate glyphosate acid and the base component to partially evaporate the water from the reaction mass and form a paste containing the water-soluble salt of glyphosate acid. The paste formed has a moisture content of from about 2% to about 20% by weight. A dicarboxylate component is added to the reaction mass and/or to the paste.

In another embodiment, the process for preparing the water-soluble pesticidal composition comprises mixing a glyphosate component comprising one or more water-soluble salts of glyphosate acid and a dicarboxylate component to form a dry pesticidal composition comprising one or more water-soluble salts of glyphosate acid and the dicarboxylate component. The glyphosate component optionally contains sources of glyphosate other than the water-soluble salt of glyphosate acid provided that at least about 50% by weight a.e. of the glyphosate component is one or more water-soluble salts of glyphosate acid.

In a further embodiment, a process is provided for preparing a pesticide enhancer composition useful in enhancing the efficacy of a pesticide composition containing a glyphosate component. The enhancer composition comprises a salt of a dicarboxylic acid and a surfactant component and is prepared by combining a dicarboxylate component comprising the dicarboxylic acid, a base component and a surfactant component in a reactor. The dicarboxylic acid and the base component are thereby caused to react and form the enhancer composition comprising the salt of the dicarboxylic acid and the surfactant component.

Other objects and features of this invention will be in part apparent and in part pointed out hereinafter.

DETAILED DESCRIPTION OF THE INVENTION

Figure 1:
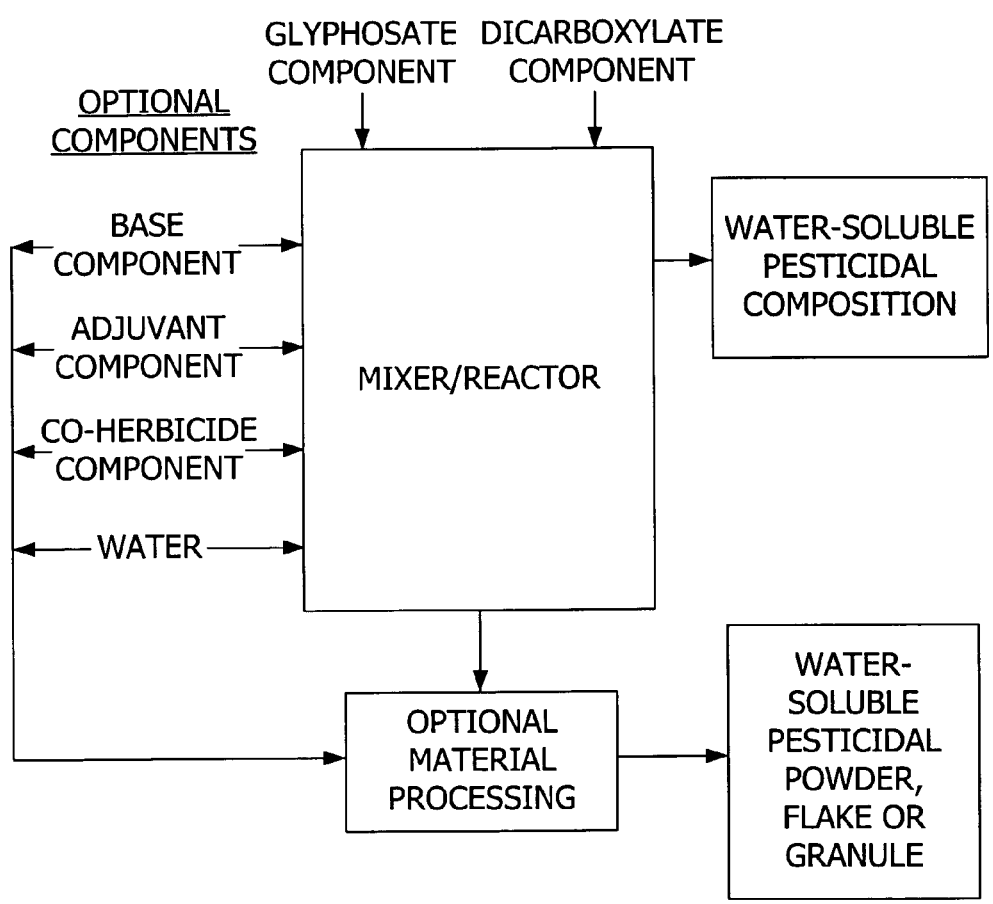
FIG. 1 shows a process flow diagram of a process for combining a glyphosate component and a dicarboxylate component and optionally a base component, an adjuvant component, a co-herbicide component and/or water to form a water-soluble pesticidal composition.

In accordance with the present invention, a process has been discovered whereby a glyphosate component and a dicarboxylate component and optionally water, an adjuvant component and/or a co-herbicide component are combined and processed in a manner to form a dry, water-soluble, pesticidal composition. A "dry" formulation herein is a composition that is solid, usually particulate, wherein particles are either aggregated as in a granular composition or non-aggregated as in a powder. The word "dry" in this context does not imply that the composition is necessarily free of water or other liquid, only that it is dry to the touch. Dry compositions can contain up to about 5% by weight of water, but more typically the moisture content (i.e., water content) is less than about 1% by weight, for example about 0.5% by weight or lower.

In another aspect of the present invention, a dicarboxylate component may be combined with an adjuvant, such as a surfactant, and optionally water to form a pesticide enhancer composition that may be added to a glyphosate component-containing pesticidal composition to enhance the performance of the pesticidal composition.

In general, the process for combining and processing the various components of either composition may be carried out in a batch or a continuous manner and may bring together solid, liquid and/or gaseous phase components.

In one embodiment, the glyphosate component comprising a water-soluble salt of glyphosate acid and the dicarboxylate component along with any optional components are combined in the requisite proportions in a suitable mixing apparatus to form the dry pesticidal composition.

Typically, all or a portion of the glyphosate component and/or the dicarboxylate component is in the form of an acid, and the components are combined and the acid in the mixture neutralized with a base component in a vessel or reactor suitable for the neutralization reaction. The mixing and neutralization steps may be carried out serially or simultaneously. Alternatively, acid present in the glyphosate component and/or dicarboxylate component may be neutralized prior to combining the components of the composition. The mixture of the glyphosate component and the dicarboxylate component may be subjected to further downstream processing steps to produce a dry, water-soluble pesticidal formulation of the desired composition in the form of a powder, granular or flake product. Optional components, such as water, one or more adjuvants or a co-herbicide may be added to the mixture of the glyphosate component and dicarboxylate component prior to or during any acid neutralization step as well as during further downstream processing of the mixture of the glyphosate component and the dicarboxylate component.

I. Components of the Mixture

A. Glyphosate Component

The glyphosate component may be glyphosate acid, a water-soluble salt of glyphosate acid, an ester of glyphosate acid or a mixture thereof. Where the glyphosate component comprises a mixture of glyphosate acid, one or more water-soluble salts of glyphosate acid and/or one or more esters of glyphosate acid, they may be added separately to the other components of the mixture or they may first be blended together.

In general, suitable water-soluble salts of glyphosate acid include mono-basic salts and may include some portions of di- and/or tri- basic salts. For example, the glyphosate component may include an ammonium salt of glyphosate acid, an alkali metal salt of glyphosate acid (e.g., sodium glyphosate or potassium glyphosate), an alkaline earth metal salt of glyphosate acid (e.g., magnesium glyphosate or calcium glyphosate), an alkylamine salt of glyphosate acid (e.g., mono-isopropylamine glyphosate salt) or a mixture of two or more water-soluble salts of glyphosate acid. Typically, the glyphosate component is added as glyphosate acid, an ammonium salt of glyphosate acid (e.g., a mono-ammonium salt of glyphosate acid) or a mixture thereof and is accompanied by small quantities of impurities typically found in and produced during the manufacture of such materials.

The glyphosate component may be added as a dry particulate solid, a moist particulate solid (e.g., glyphosate acid wet cake) or as part of a slurry. Where the glyphosate component is added in a slurry, the glyphosate component may be mixed with water and/or a liquid adjuvant component to form the slurry. While not narrowly critical to the present invention, the concentration of the glyphosate component in such a slurry may be varied depending on the desired total quantity of water and/or adjuvant component in the mixture and the amount of water and/or adjuvant that is to be added separately or with one or more of the other components of the mixture.

B. Dicarboxylate Component

The dicarboxylate component may be a dicarboxylic acid (hydrated or anhydrous), a derivative of a dicarboxylic acid, or may be a combination of two or more dicarboxylic acids and/or derivatives thereof. Where the dicarboxylate component comprises a mixture of two or more dicarboxylic acids and/or derivatives thereof, they may be added separately to the other components of the mixture or they may first be blended together.

In general, suitable dicarboxylic acids include oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid (also known as 3-hydroxy malonic acid) suberic acid, azelaic acid, sebacic acid, 1,12-dodecanedioic acid, 1,13-tridecanedioic acid, glutamic acid, phthalic acid, isophthalic acid and terephthalic acid.

Suitable derivatives of dicarboxylic acids include anhydrides, esters (e.g., mono- and di-esters), amides, halides and salts (e.g., mono- and di-salts) of dicarboxylic acids as well as precursors of any of the aforementioned dicarboxylic acids. Suitable esters include methyl, ethyl, propyl and butyl esters and esters formed when one or more dicarboxylic acids reacts with one or more surfactants. Solid dicarboxylic acids typically have poor solubility in water. Typically, therefore, when a portion or all of the dicarboxylate component is a dicarboxylic acid, the acid may be combined with a base component to form a salt of the dicarboxylic acid. Suitable salts of dicarboxylic acids include, for example, alkali metal salts such as sodium and potassium salts, alkanolamine salts and alkylamine salts such as IPA salts.

Precursors of dicarboxylic acids can be used as the dicarboxylate component in the preparation of the compositions of the invention. Terminally functionalized hydroxyacids, oxoacids, $\alpha,\omega$-dihydroxyalkanes, dinitriles, and dioxoalkanes are easily oxidized to dioic acids. $\alpha,\omega$-aminoacids, haloacids, and dihalides are hydrolyzable to hydroxyacids or dihydroxides which are then oxidized. Precursors for use in the invention include, for example, oxalic acid precursors (glycolic acid, glyoxylic acid (and salts, e.g., oxaloacetate), glyoxal sodium bisulfite, oxalyl halides, ethylene glycol, glyoxal, 1,2-dihaloethane), adipic acid precursors (e.g., $\alpha$-aminoadipic acid, cyclohexanol, cyclohexanone, cyclohexane), malonic acid precursors (e.g., malic acid, malonic dialdehyde, methylmalonic acid, cyanoacetic acid, diethyl malonate, malonyl Coenzyme A, acetyl CoA, acetate, butyrate), malic acid precursors (ketoglutaric acid, 2-oxoglutaric), succinic acid precursors (e.g., malic acid, malate, maleic acid, ketoglutaric acid, succinic acid dimethyl ester, succinic dialdehyde, L-glutamate, oxaloacetate, fumarate), and glutaric acid precursors (e.g., glutaric dialdehyde, glutaronitrile, cyclopentane, cyclopentanone, lysine, tryptophan, hemiamido glutarate, amidomethyl glutarate).

Oxalic acid and derivatives thereof have proven most effective in improving the performance of the pesticidal compositions of the invention. Accordingly, the dicarboxylate component preferably comprises oxalic acid or derivatives thereof, such as salts of oxalic acid or esters of oxalic acid. Suitable salts of oxalic acid include potassium oxalate, di-potassium oxalate, sodium oxalate, disodium oxalate, ammonium oxalate, di-ammonium oxalate, diethanolamine oxalate, dimethylamine oxalate, alkanolamine salts of oxalic acid, and lower alkylamine salts of oxalic acid. Suitable esters of oxalic acid include methyl, ethyl, propyl and butyl esters, alkylamine and alkoxylated alkylamine esters (e.g., cocoamine oxalate, stearylamine oxalate, tallowamine oxalate, alkoxylated cocoamine oxalate, alkoxylated stearylamine oxalate, alkoxylated tallowamine oxalate). Alkoxylated groups include, for example, methoxy, ethoxy and propoxy.

The dicarboxylate component may be added as a dry solid, a melt or as part of a slurry. Where the dicarboxylate component is added in a slurry, the dicarboxylate component may be mixed with water and/or a liquid adjuvant component to form the slurry. While not narrowly critical to the present invention, the concentration of the dicarboxylate component in such a slurry may be varied depending on the desired total quantity of water and/or adjuvant component in the mixture and the amount of water and/or adjuvant that is to be added separately or with one or more of the other components of the mixture.

Where the dicarboxylate component is added as a melt, it should be noted that the melt will typically crystallize upon cooling. Accordingly, it may be preferable to maintain the temperature of the mixture above the melt temperature of the dicarboxylate component until a substantially homogeneous mixture with the glyphosate component and other components of the mixture is attained.

Where the dicarboxylate component is in the form of particulates (e.g., as a dry solid or as part of a slurry), the particle size distribution of the dicarboxylate component is typically similar to the particle size distribution of the glyphosate component in order to promote homogeneity and avoid segregation in the mixture. However, the particle size distribution of the dicarboxylate component and the glyphosate component may vary significantly without departing from the scope of the present invention. Nevertheless, it should be noted, that smaller particles typically become airborne more readily and, depending on the toxicity of the dicarboxylate component, may result in industrial hygiene exposure problems. On the other hand, larger particles may adversely effect downstream processing steps such as extrusion granulation and/or reduce the solubility of the final product. The glyphosate component and/or dicarboxylate component may be selected, or may be subjected to any unit operation known to persons skilled in the art for either reducing the particle size (e.g., milling) or to remove oversize or under-size particles from the glyphosate component and/or dicarboxylate component (e.g., sifting).

C. Water

Water addition is not required in those embodiments of the present invention in which the glyphosate component comprising a water-soluble salt of glyphosate acid, dicarboxylate component and optionally an adjuvant component and/or co-herbicide component are dry blended to form a particulate pesticidal composition. However, in those embodiments where acid present in the mixture of the glyphosate component and dicarboxylate component is neutralized with a base component, a solvent is typically added to the mixture of the glyphosate component and the dicarboxylate component prior to or during the neutralization step to promote the neutralization reaction. Typically, the solvent added is water, however, other solvents such as organic solvents, including $C_1$–$C_4$ alcohols, toluene or acetone may be used in place of or in addition to water without departing from the scope of the present invention. Water or other solvent may be added separately or in combination with one or more of the other components (e.g., as part of a slurry in which the glyphosate component or dicarboxylate component is suspended). Finally, water may be added as a binding agent in material processing steps as described in more detail below.

In general, the amount of water added to a reactor in which the neutralization step is carried out is at least about 2% by weight of all of the components added to the reactor (i.e., at least about 2% by weight of the neutralization reaction mass). Water may be produced during the neutralization step and thereby added to the reaction mass. The amount of water added to the reactor, including any water produced by the neutralization reaction, may vary depending on the neutralization and/or material processing steps as discussed in more detail below. When the neutralization step is carried out in a solid state, the amount of water added is generally from about 2% to about 40% by weight, more typically from about 2% to about 25% by weight of all of the components added to the reactor for the neutralization step. When the neutralization step is carried out in a liquid state (i.e., the neutralization reaction mass is in the form of a slurry or solution), the water concentration may be substantially higher than 40% by weight of all the components combined in the reactor. If an organic solvent is added to the reactor in place of or in combination with water, the amount of water present may be substantially less than 2% by weight or water may not be present at all.

D. Adjuvant Component

An adjuvant component may be optionally included in the mixture of the glyphosate component and the dicarboxylate component. The adjuvant component may be a single adjuvant or it may comprise two or more adjuvant materials. A portion or all of the adjuvant component may be added as a solid, melt, solution or slurry. Where two or more adjuvant materials are used, they may be added separately to the mixture or they may first be blended together and the blend may then be added to the mixture or combined with one or more of the other components and then added to the mixture.

In general, the adjuvant component added to the mixture may be a surfactant component, anti-foaming agent, filler, humectant, symptomatology agent, desiccant, lubricant, scavenger or a mixture thereof.

Dry pesticidal compositions in accordance with the present invention typically contain a surfactant component in addition to the water-soluble salt of glyphosate acid and the dicarboxylate component. The surfactant component may comprise one or more nonionic surfactants, cationic surfactants, anionic surfactants, amphoteric surfactants, silicone surfactants, fluorocarbon surfactants and mixtures thereof. Surfactants are important components of glyphosate formulations because, when a glyphosate formulation is diluted, dissolved or dispersed in water for application by spraying to foliage of plants, the surfactants assist in retention of droplets of the spray by the foliage, adhesion of the spray droplets to the foliar surface and penetration of the glyphosate through the hydrophobic cuticle that covers the foliar surface, by these means and possibly in other ways enhancing herbicidal effectiveness of the glyphosate spray. Specific surfactant types differ greatly in the degree to which they enhance herbicidal effectiveness of glyphosate, and it is therefore important to select a suitable surfactant or combination of surfactants, as demonstrated by Wyrill & Burnside, Weed Science 25, 275–287, 1977.

Examples of suitable nonionic surfactants include alkylpolyglucosides; glycerol esters such as glyceryl monolaurate, and ethyoxylated glyceryl monococoate; ethoxylated castor oil; ethoxylated reduced sugar esters such as polyoxyethylene sorbitol monolaurate; esters of other polyhydric alcohols such as sorbitan monolaurate and sucrose monostearate; ethoxylated amides such as polyoxyethylene cocoamide; ethoxylated esters such as monolaurate of polyethylene glycol 1000 and dilaurate of polyethylene glycol 6000; ethoxylated alkyl or arylphenols such as nonylphenol alkoxylate, octylphenol ethoxylates, dodecylphenol ethoxylates, dinonylphenol ethoxylates and tristyrylphenol ethoxylates; alcohol ethoxylates such as fatty alcohol ethoxylates (e.g., oleyl alcohol ethoxylate), tridecylalcohol ethoxylates and other alcohol ethoxylates such as NEODOLS and oxoalcohol ethoxylates; and ethylene oxide/propylene oxide copolymers such as PLURONIC type, TETRONIC type, or TERGITOL XH type.

Examples of suitable cationic surfactants include alkylamine ethoxylates (including etheramines and diamines) such as tallowamine alkoxylate, cocoamine alkoxylate, etheramine alkoxylate, tallow ethylenediamine alkoxylate and amidoamine ethoxylates; alkylamine quaternary amines such as alkoxylated quaternary amines (e.g., ethoxylated quaternary amines or propoxylated quaternary amines); alkylamine acetates such as tallowamine acetate or octylamine acetate; and amine oxides such as ethoxylated amine oxides (e.g., N,N-bis(2-hydroxyethyl)cocoamine Boxide), nonethoxylated amine oxides (e.g., cethyldimethylamine Boxide) and amidoamine oxides.

Examples of suitable anionic surfactants include fatty soaps such as ammonium tallowate and sodium stearate; alkyl sulfates such as sodium $C_{8-10}$ alcohol sulfate, sodium oleyl sulfate, and sodium lauryl sulfate; sulfated oils such as sulfated castor oil; ether sulfates such as sodium lauryl ether sulfate, ammonium lauryl ether sulfate, and ammonium nonylphenol ether sulfate; sulfonates such as petroleum sulfonates, alkylbenzene sulfonates (e.g., sodium (linear) dodecylbenzene sulfonate or sodium (branched) dodecylbenzene sulfonate), alkylnapthalene sulfonates (e.g., sodium dibutylnapthalene sulfonate), alkyl sulfonates (e.g., alpha olefin sulfonates), sulfosuccinates such as dialkylsulfosuccinates (e.g., sodium dioctylsulfosuccinate) and monoalkylsulfosuccinate and succinamides (e.g., disodium laurylsulfosuccinate and disodium N-alkylsulfosuccinamate); sulfonated amides such as sodium N-methyl N-coco taurate; isethionates such as sodium cocoyl isethionate; sarcosinates such as N-lauroyl sarcosine; and phosphates such as alkylether alkoxylate phosphates and alkylarylether ethoxylated phosphates.

Examples of suitable amphoteric surfactants include betaines such as simple betaines (e.g., cocodimethylbetaine), sulfobetaines, amidobetaines, and cocoamidosulfobetaines; imidazolinium compounds such as disodium lauroamphodiacetate, sodium cocoamphoacetate, sodium cocoamphopropionate, disodium cocoaminodipropionate, and sodium cocoamphohydoxypropyl sulfonate; and other amphoteric surfactants such as N-alkyl, N,-bis(2-hydroxyethyl)glycine and alkylaminedipropionates.

Examples of suitable silicone surfactants include ethoxylated or propoxylated silicone based surfactants, e.g., SILLOUETTE L-77 or BREAK-THRU S-200.

Examples of suitable fluorocarbon surfactants include anionic fluorinated surfactants, e.g. DUPONT ZONYL FSK, amphoteric fluorinated surfactants, e.g., DUPONT ZONYL TLF-9579, and nonionic fluorinated surfactants, e.g. DUPONT ZONYL FSH.

Examples of suitable anti-foaming agents include silicones and fatty acids.

Examples of suitable fillers include di-ammonium phosphate, sodium phosphate, ammonium sulfate, sodium chloride, sodium sulfate, dyes or pigments, urea, sucrose and potassium phosphate.

Examples of suitable humectants include ethylene glycol, propylene glycol and glucose.

Examples of suitable symptomatology agents include nonanoic fatty acid polycarboxylic acids such as citric acid and ethylendiaminetetraacetic acid (EDTA).

Examples of suitable desiccants include anhydrous calcium sulfate.

Examples of suitable lubricants include fatty acids such as oleic acid; silicon oils such as polydimethylsiloxane; fatty esters such as corn oil, sugars and reduced sugars.

Examples of suitable scavengers include sodium sulfite and ascorbic acid.

In one embodiment, a portion or all of the adjuvant component included in the mixture of the glyphosate component and the dicarboxylate component is a surfactant component comprising a cationic surfactant, amphoteric surfactant or selected from the class of nonionic surfactants known as alkyl polyglycosides (APGs) and polyoxyethylene $C_{16-22}$ alkylethers. Polyoxyethylene derivatives of such cationic and amphoteric surfactants are particularly preferred. The term "alkyl" is used in the present context to denote one or more linear or branched, saturated or unsaturated hydrocarbyl chains having, unless otherwise specified, about 8 to about 22 carbon atoms. Other materials, including water and/or glycols, can optionally be admixed with the adjuvant or adjuvants prior to addition to the mixture.

Where acid in the glyphosate component and/or dicarboxylate component is neutralized with a base component to form the corresponding salt, all or a portion of the adjuvant component may be added to the glyphosate component, dicarboxylate component and/or mixture thereof prior to neutralization, during neutralization, or after neutralization. In general, all of the adjuvant component is added prior to any downstream material processing steps (e.g., pan granulation, drum drying, spray drying, extrusion, etc.).

In one embodiment, a portion of the adjuvant component is added during the neutralization step with the remainder being added after neutralization as discussed in more detail below with regard to the neutralization process. Typically, the adjuvant component may be added in various amounts to the mixture and when added as part of the neutralization reaction may be added in various amounts and at various locations in the process, depending upon the adjuvant and the desired composition and properties of the final product.

E. Co-herbicide Component

The glyphosate component may optionally be combined with one or more co-herbicides in the mixture. If included, a co-herbicide component may be added to the mixture as an acid and subsequently neutralized by a base component during the neutralization step (e.g., simultaneously with the neutralization of acid in the glyphosate component and/or dicarboxylate component) or may be added to the mixture already neutralized and in the form of a salt.

Examples of suitable co-herbicides include acifluorfen, asulam, benazolin, bentazon, bilanafos, bromacil, bromoxynil, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr. Alternatively, any of these co-pesticidal active ingredients can be added already neutralized and in the form of a salt.

Salts of the above co-herbicides are generally water-soluble and the final product of the process is a water-soluble pesticidal composition. Optionally, a water-insoluble, co-pesticidal active ingredient can be included in the mixture, in which case the end-product of the process is a water-dispersible pesticidal formulation. Examples of suitable water-insoluble co-herbicides useful in this embodiment of the invention include acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlorotoluron, chlornitrofen, chlorotoluron, chlorpropham, chlorsulfuron, chlorthaldimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifopbutyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfopmethyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobacmethyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vernolate.

F. Base Component

As mentioned above and discussed in greater detail below, if a portion or all of the glyphosate component is glyphosate acid and/or if a portion or all of the dicarboxyate component is one or more dicarboxylic acids, a base component may be added to the mixture of the glyphosate component and dicarboxylate component in a suitable reactor vessel such that at least a portion of the glyphosate acid and/or dicarboxylic acid is neutralized to the corresponding salt by the base component in a neutralizing step.

In general, the base component used in the neutralization step may be added to the reactor vessel as a solid, liquid or gas and may be an alkali metal hydroxide such as sodium hydroxide or potassium hydroxide, an alkaline earth metal hydroxide such as magnesium hydroxide or calcium hydroxide, carbonates of alkali metals or alkaline earth metals such as sodium carbonate or sodium bicarbonate, alkali metal phosphates such as sodium phosphate, disodium phosphate, trisodium phosphate, potassium phosphate, ammonium phosphate or di-ammonium phosphate, or ammonia, ammonium carbonate, ammonium bicarbonate, ammonium hydroxide or mixtures thereof.

In general, the amount of base component added to the reactor in which the neutralization step is carried out is determined based on the desired degree of neutralization of the glyphosate acid and/or dicarboxylic acid present in the components fed to the process and can be readily determined. The amount of base component added may be such that the glyphosates acid and/or dicarboxylic acid is either over neutralized or under neutralized. Typically the amount of base component added to neutralize glyphosate acid is from about 0.8 to about 1.25, more typically from about 0.9 to about 1.1 and in one embodiment from about 0.95 to about 1.05 moles of base component per mole of glyphosate acid. In those embodiments where the dicarboxylate component comprise a dicarboxylic acid, an additional amount of base may be added to neutralize all or a portion of the dicarboxylic acid as readily determined by one skilled in the art. For example, when neutralizing a mixture of glyphosate acid and oxalic acid using ammonia as the base component, in addition to the roughly stoichiometric amount of ammonia added to neutralize the glyphosate acid, an additional amount of ammonia, typically from about 1 to about 2 moles of ammonia per mole of oxalic acid, is added to neutralize the oxalic acid. In one embodiment glyphosate acid is over neutralized and then combined with dicarboxylic acid to neutralize a portion or all of the dicarboxylic acid. In another embodiment, dicarboxylic acid is over neutralized and then combined glyphosate acid to neutralize a portion or all of the glyphosate acid.

II. Dry Pesticidal Composition

The dry pesticidal compositions made in accordance with the present invention contain various combinations of the above-described components in amounts sufficient to enhance the resulting efficacy of the composition. Those skilled in the art can readily adapt the processes as disclosed herein so as to produce a dry pesticidal formulation of the desired composition including a glyphosate component, a dicarboxylate component and optionally an adjuvant component. For most applications, the glyphosate component will comprise one or more water-soluble salts of glyphosate acid and the dry pesticidal composition will include a surfactant component.

The molar ratio of glyphosate component to dicarboxylate component is from about 25:1 to about 1:4, preferably from about 11:1 to about 1:4, more preferably from about 8:1 to about 1:3, and most preferably from about 7:1 to about 1:1.5 on an acid equivalent, or a.e., basis. For a dicarboxylate component comprising oxalic acid or a derivative thereof, the weight ratio of glyphosate component to oxalic acid is preferably from about 20:1 to about 1:2, more preferably from about 15:1 to about 1:1.25, and most preferably from about 13:1 to about 1.2:1 on an acid equivalent basis. One skilled in the art can extrapolate the above molar ratios derived for oxalic acid to determine the appropriate weight ratio for any other dicarboxylate component.

The adjuvant component is typically present in the composition such that the total amount of adjuvant component is generally no greater than about 50% by weight, typically from about 5% to about 50% and more typically from about 5% to about 25% by weight of all of the composition. The weight ratio of adjuvant component to glyphosate component on a glyphosate acid equivalent basis may be at least about 1:500, at least about 1:250 or even at least about 1:100. In some embodiments, the weight ratio of adjuvant component to glyphosate component on a glyphosate acid equivalent basis may be even greater with the weight ratio being at least about 1:75, at least about 1:50, at least about 1:25, at least about 1:10, at least about 1:5 or even about 1:2. In general, however, the weight ratio of adjuvant component to glyphosate component on a glyphosate acid equivalent basis will be less than about 1:1, and more typically less than about 1:2, with weight ratios of from about 1:10 to about 1:250, from about 1:25 to about 1:150 or even from about 1:50 to about 1:100 being even more typical. The weight ratio of total surfactant to dicarboxylate component is from about 10:1 to about 1:10, more preferably from about 5:1 to about 1:3, and most preferably from about 3:1 to about 1:2 on an acid equivalent basis.

The dry pesticidal compositions of the present invention preferably comprise a glyphosate component in a concentration of from about 10 to about 90% by weight a.e. of the composition, a surfactant component in a concentration up to about 50% by weight of the composition, and a dicarboxylate component in a concentration of from about 1% to about 60% by weight a.e. of the composition. More preferably, the compositions comprise a glyphosate component in a concentration from about 30% to about 80% by weight a.e. of the composition, a surfactant component in a concentration of from about 5% to about 25% by weight of the composition, and a dicarboxylate component in a concentration from about 3% to about 50% by weight a.e. of the composition. In another embodiment, the compositions comprise a glyphosate component in a concentration from about 30% to about 80% by weight a.e. of the composition, a surfactant component in a concentration from about 5% to about 25% by weight of the composition, and a dicarboxylate component in a concentration from about 5% to about 50% by weight a.e. of the composition.

More preferably, the dry pesticidal compositions comprise a glyphosate component in a concentration from about 35% to about 80% by weight a.e. of the composition, a surfactant component in a concentration from about 5% to about 25% by weight of the composition, and a dicarboxylate component in a concentration from about 5% to about 40% by weight a.e. of the composition. Even more preferably, the compositions comprise a glyphosate component in a concentration from about 50% to about 80% by weight a.e. of the composition, a surfactant component in a concentration from about 7.5% to about 25% by weight of the composition, and a dicarboxylate component in a concentration from about 10% to about 30% by weight a.e. of the composition. Most preferably, the compositions comprise a glyphosate component in a concentration from about 50% to about 80% by weight a.e. of the composition, a surfactant component in a concentration from about 7.5% to about 20% by weight of the composition, and a dicarboxylate component comprising oxalic acid or a salt or ester thereof in a concentration from about 10% to about 25% by weight a.e. of the composition, or the compositions comprise a glyphosate component in a concentration from about 50% to about 72% by weight a.e. of the composition, a surfactant component in a concentration from about 7.5% to about 20% by weight of the composition, and a dicarboxylate component comprising oxalic acid or a salt or ester thereof in a concentration from about 10% to about 25% by weight a.e. of the composition. In yet another embodiment, the compositions comprise a glyphosate component in a concentration from about 35% to about 80% by weight a.e. of the composition, a surfactant component in a concentration from about 5% to about 25% by weight of the composition, and a dicarboxylate component in a concentration from about 3% to about 40% by weight a.e. of the composition. Even more preferably, the compositions comprise a glyphosate component in a concentration from about 50% to about 80% by weight a.e. of the composition, a surfactant component in a concentration from about 7.5% to about 25% by weight of the composition, and a dicarboxylate component in a concentration from about 3% to about 30% by weight a.e. of the composition. Most preferably, the compositions comprise a glyphosate component in a concentration from about 50% to about 80% by weight a.e. of the composition, a surfactant component in a concentration from about 7.5% to about 20% by weight of the composition, and a dicarboxylate component comprising oxalic acid or a salt or ester thereof in a concentration from about 3% to about 25% by weight of the composition, or the compositions comprise a glyphosate component in a concentration from about 50% to about 77% by weight a.e. of the composition, a surfactant component in a concentration from about 7.5% to about 20% by weight of the composition, and a dicarboxylate component comprising oxalic acid or a salt or ester thereof in a concentration from about 3% to about 25% by weight of the composition.

In a preferred embodiment, the dry pesticidal composition of the present invention contain oxalic acid or an anhydride, ester, amide, halide, salt or precursor thereof as the dicarboxylate component in combination with at least one salt of a polycarboxylic acid, such as sodium citrate or the sodium salt of EDTA. Such mixtures are especially preferred for use in dry pesticidal compositions containing a relatively low concentration of glyphosate component to reduce any eye irritancy which may otherwise result from relatively high concentrations of oxalic acid.

III. Preparation of the Dry Pesticidal Composition

A. Mixing

As shown generally in FIG. 1, the process of the present invention includes combining and intimately mixing a glyphosate component with a dicarboxylate component and optionally water, an adjuvant component and/or a co-herbicide component in a mixer to form a water-soluble pesticidal composition. The mixture may be further processed in one or more material processing steps to form a powder, flake or granular pesticidal composition. If the mixture is subjected to the material processing step(s), a portion or all of the water, adjuvant component and/or co-herbicide component may be added during the material processing step(s).

Figure 2:
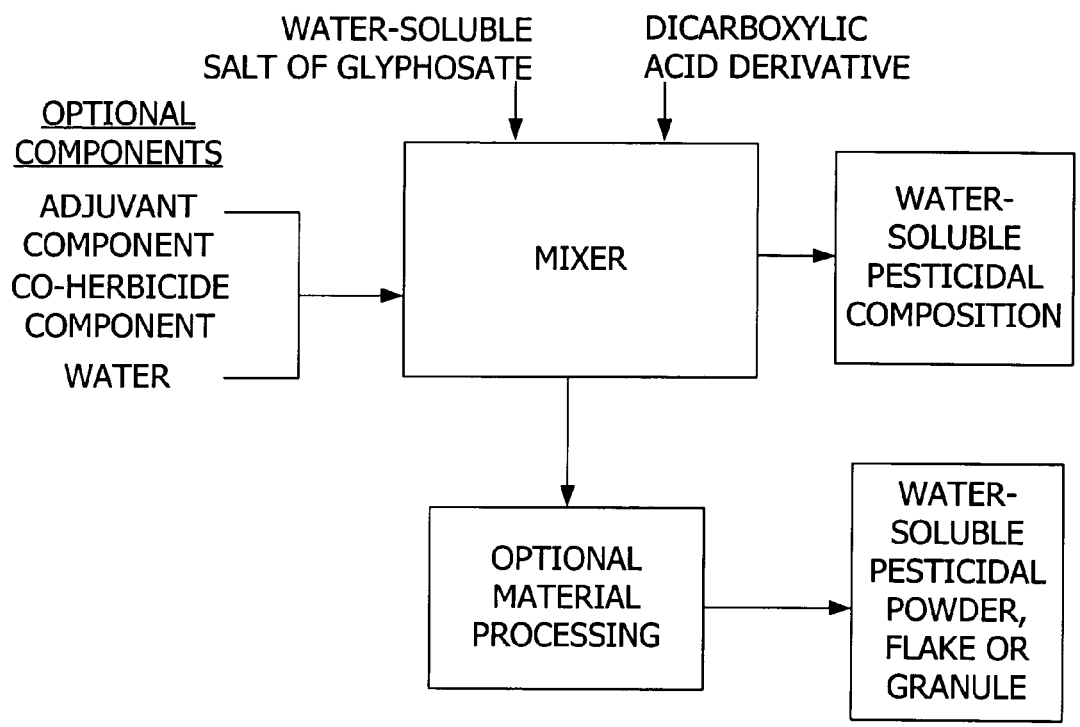
FIG. 2 shows a process flow diagram of a process for combining a water-soluble salt of glyphosate acid and a dicarboxylic acid derivative and optionally an adjuvant component, a co-herbicide component and/or water to form a water-soluble pesticidal composition.

In one embodiment, shown in FIG. 2, a glyphosate component comprising a water-soluble salt of glyphosate acid and/or an ester of glyphosate acid, is combined with a dicarboxylate component and optionally water, an adjuvant component and/or a co-herbicide component to form a water-soluble particulate pesticidal composition. For example, a glyphosate component comprising at least about 50% by weight a.e., at least about 75% by weight a.e., at least about 90% by weight a.e. or more of a water-soluble salt or ester of glyphosate acid is combined with a dicarboxylate component and optionally water, an adjuvant component and/or a co-herbicide component in the desired proportions in a suitable mixing apparatus, such as a food processor, Hobart mixer, ribbon blender, kneader or the like. In accordance with one embodiment of the invention, the glyphosate component combined with the dicarboxylate component consists essentially of a water-soluble salt of glyphosate acid. The mixture is agitated until it appears homogeneous. Mixing time in this step is dependent on the mixing device used and on the quantity and composition of the mixture being prepared. The process for mixing the glyphosate component, dicarboxylate component and optionally water, an adjuvant component and/or a co-herbicide component may be carried out as a batch or continuous process in either a solid or liquid state. The resulting mixture of a water-soluble salt or ester of glyphosate acid, dicarboxylate component and optionally an adjuvant component and/or co-herbicide component may then be subjected to one or more material processing steps to form a granular, powder or flake pesticidal composition as described in more detail below. The resulting granular, particulate or flake product may be dried in any suitable drying device such as a fluid bed dryer or the like to a desired lower moisture content.

Figure 3:
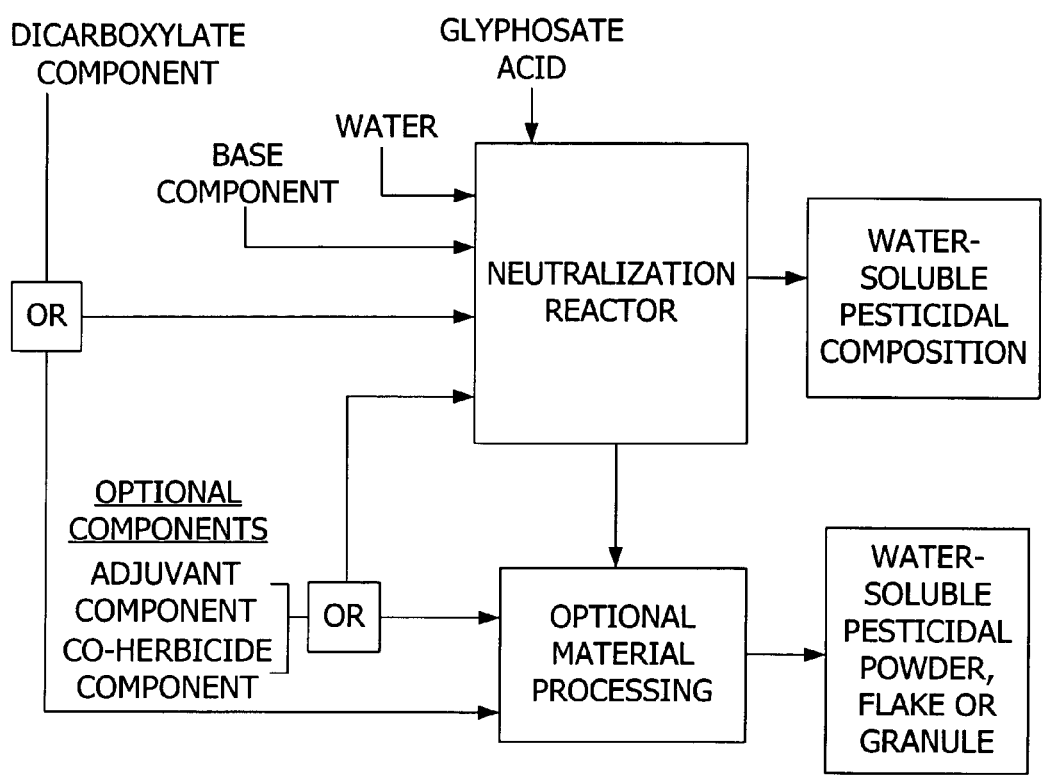
FIG. 3 shows a process flow diagram of a process for combining a glyphosate component, a portion or all of which is glyphosate acid, a dicarboxylate component, a base component, water and optionally an adjuvant component and/or a co-herbicide component to form a water-soluble pesticidal composition.
Figure 4:
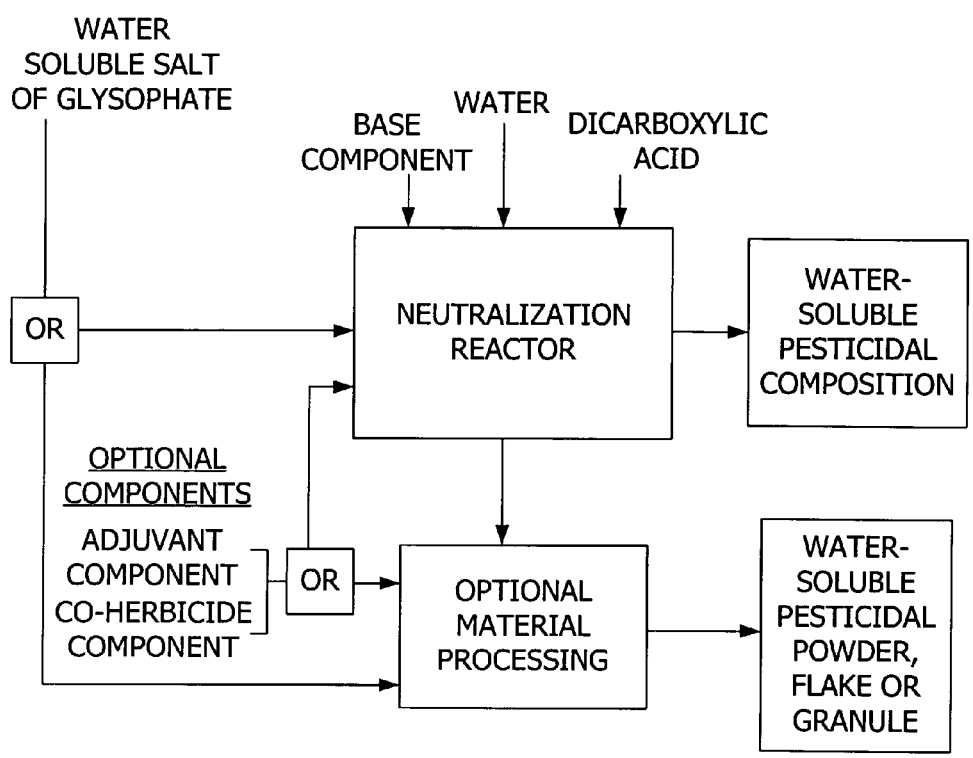
FIG. 4 shows a process flow diagram of a process for combining a water-soluble salt of glyphosate acid, a dicarboxylate component, a portion or all of which is a dicarboxylic acid, a base component, water and optionally an adjuvant component and/or a co-herbicide component to form a water-soluble pesticidal composition.
Figure 5:
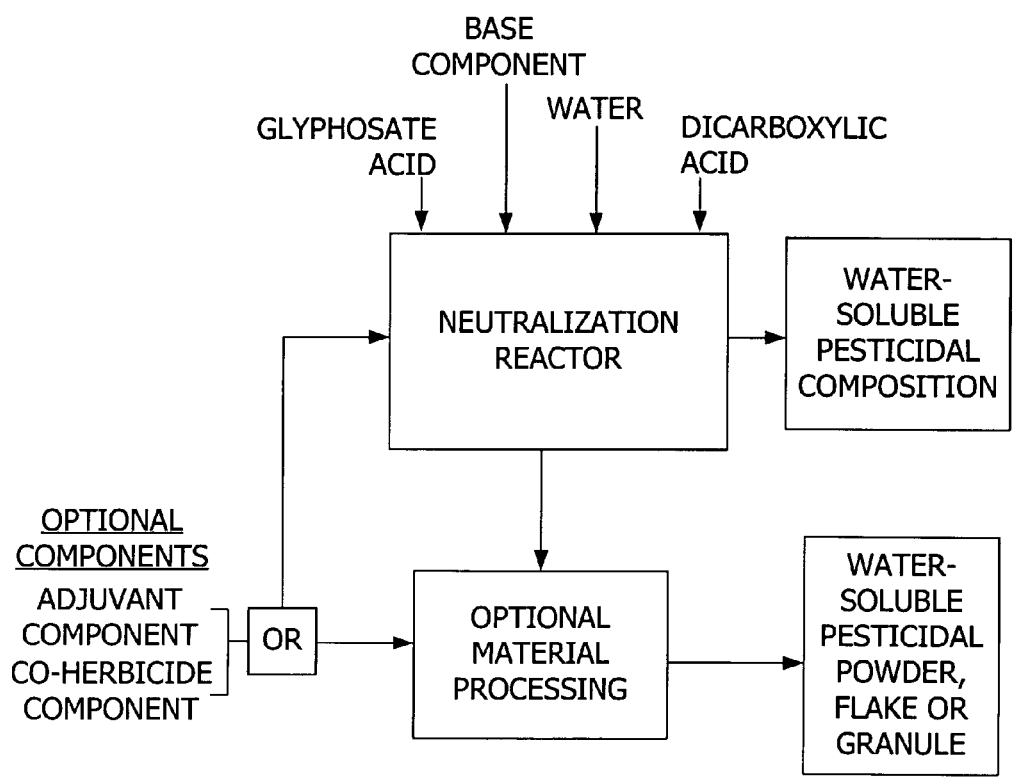
FIG. 5 shows a process flow diagram of a process for combining a glyphosate component, a portion or all of which is glyphosate acid and a dicarboxylate component, a portion or all of which is dicarboxylic acid, a base component, water and optionally an adjuvant component and/or a co-herbicide component to form a water-soluble pesticidal composition.

As shown in FIGS. 3–5, embodiments wherein the glyphosate component and/or the dicarboxylate component utilized is in part or in whole an acid, typically include addition of a base component to at least partially neutralize the acid present. That is, if a portion or all of the glyphosate component is glyphosate acid and/or if a portion or all of the dicarboxyate component is a dicarboxylic acid, a base component may be added to these components in a suitable reactor vessel such that at least a portion of the glyphosate acid and/or dicarboxylic acid is neutralized to the corresponding salt by the base component to provide a pesticidal product of the desired composition. The mixing of the glyphosate component and dicarboxylate component may be carried out prior to introduction into the neutralization reactor (i.e., pre-mixed), during or after the neutralization of acid in one or more of the components. In one embodiment, a glyphosate component, a portion or all of which is glyphosate acid, may be at least partially neutralized with a base component and combined with a dicarboxylate component as shown in FIG. 3. In another embodiment, a dicarboxylate component, a portion or all of which is a dicarboxylic acid, may be at least partially neutralized with a base component and combined with a water-soluble salt of glyphosate acid as shown in FIG. 4. In a still further embodiment, a glyphosate component, a portion or all of which is glyphosate acid and a dicarboxylate component, a portion or all of which is a dicarboxylic acid, may be combined and the acids at least partially co-neutralized with a base component as shown in FIG. 5. The addition of a base component is discussed in more detail below with regard to the neutralization step.

B. Neutralization

1. Neutralization of the Glyphosate Component

As depicted in FIG. 3, glyphosate acid may be combined with a base component such that the glyphosate acid is neutralized by the base component to form a water-soluble salt of glyphosate. A dicarboxylate component is combined with the glyphosate acid before, during or after the neutralization reaction occurs. Water is introduced before or during the neutralization step. Optionally, an adjuvant component and/or a co-herbicide component may also be introduced before, during or after the neutralization step. That is, the neutralization of glyphosate acid may be carried out separately or in the presence of the dicarboxylate component and/or the optional components discussed above. The amount of water added to the neutralization reactor may be varied such that the reaction mass formed is either in a solid state or a liquid state.

In the solid state reaction, the total amount of water added to the reactor is generally at least about 2% by weight of all the components added to the reaction mass and generally no more than about 40% by weight of all of the components added to the reaction mass and typically no greater than about 25% by weight of all of the components added to the reaction mass, thereby forming a wet, solid state reaction mass. Advantageously, the exothermic heat of reaction of the glyphosate acid and the base component causes the evaporation of water thereby reducing the moisture content of the reaction mass. Depending on the initial amount of water added to the reaction mass and the amount of water evaporated from the reaction mass, the reaction product may be a substantially dry, free flowing powder having a moisture content of no greater than about 2% by weight or may be a downstream processable paste having a moisture content of from about 2% to about 20% by weight, as described in U.S. Pat. Nos. 5,633,397 and 5,614,468, PCT Publication No. WO 02/085122 and U.S. Pat. No. 6,605,568, the entire disclosures of which are incorporated herein by reference. The term "downstream processable", as used herein, means that the paste is readily capable, upon further reduction in moisture content, if necessary, of being further processed by extrusion granulation with one or more adjuvants to form a dry granular herbicidal composition. An adjuvant component, co-herbicide component and/or base component may be added to the glyphosate acid neutralization reaction mixture prior to and/or during the reaction. In addition, the reaction product, whether as a dry powder or a paste, may be further combined with an adjuvant component, co-herbicide component and/or additional water to form an extrudable mixture. The extrudable mixture may then be extruded to form a granular product.

In embodiments where the neutralization reaction is carried out in a solid state, a particulate form of the glyphosate component is combined in a reactor with a base component and water and optionally an adjuvant component and/or co-herbicide to form a reaction mass wherein the base component reacts with the acid in the glyphosate component to form dry free-flowing water-soluble glyphosate salt or a downstream processable paste containing a water-soluble glyphosate salt. The reactor used to carry out the neutralization reaction may be any apparatus capable of mixing solid, liquid and/or gaseous materials to produce a dry, free flowing powder, paste or comparable composition. Examples of such apparatus include food mixers, planetary mixers, ribbon blenders or kneaders.

In one embodiment, the reactor is an assembly comprising a vessel in which is disposed a rotatable shaft having one or more screw elements coaxial with the shaft and bearing a plurality of radially disposed pins and/or paddles. More than one of such shafts can be present, disposed parallel to one another and rotatable in the same direction or in opposite directions. More particularly, suitable mixer/reactor apparatus for use in the practice of the present invention comprise a substantially enclosed elongate chamber having one or more, preferably one or two, rotatably disposed shafts as described above, each on an axis parallel to the elongate dimension of the chamber. The reactor chamber has at an input end an aperture suitable for introduction of the particulate glyphosate acid, at an output end an aperture suitable for discharge of the neutralization reaction product comprising a water-soluble salt of glyphosate acid, and having between the input and output ends, one or more ports suitable for introduction of a base component and water and optionally a dicarboxylate component, an adjuvant component and/or co-herbicide component. Optionally, additional ports may be present near the output end of the reactor vessel for exhaust of water vapor generated during the neutralization reaction.

Operation of the apparatus by rotation of the shafts effects: (i) feeding of the glyphosate acid into the reactor chamber through the aperture at the input end; (ii) mixing of the components to form a neutralization reaction mass; (iii) bulk movement of the neutralization reaction mass comprising the water-soluble glyphosate salt in a direction parallel to the shaft and towards the output end of the chamber; and, (iv) discharge of the neutralization reaction product from the aperture at the output end. Preferably, water and optionally a dicarboxylate component, an adjuvant component and/or co-herbicide component are injected at or near the input end of the vessel, while the base component is injected through one or more injection ports with each port being a sufficient distance from the input end to permit thorough mixing of the glyphosate acid, water and optionally a dicarboxylate component, an adjuvant component and/or co-herbicide component prior to substantial exposure of the glyphosate acid and optionally dicarboxylic acid with the base component. In one embodiment, the water and adjuvant and dicarboxylate component are pre-mixed with the glyphosate acid prior to feeding the glyphosate acid into the reaction vessel, thus enabling the base component to be injected through one or more ports located at any location within the reaction chamber.

Equipment of the type just described as suitable for carrying out the present invention (i.e., continuous single- or twin-shaft mixers/kneaders or solids processors) are commercially available, for example, from Buhler Limited (Uzwil, Switzerland), Readco Manufacturing Inc. (York, Pa.) and Werner and Pflieder Corporation (Ramsey, N.J.), in various sizes (for example, 5 cm, 13 cm, 20 cm, 25 cm, 38 cm, 62 cm, 93 cm, 125 cm and 175 cm vessel diameter) depending on the type of equipment selected and the desired throughput. With the information presented herein, one of skill in the art will find it straightforward by routine testing to establish, for any particular apparatus of the type described, a suitable shaft rotation speed (affecting glyphosate acid feed rate as well as residence time in the chamber), water feed rate, adjuvant feed rate and base component injection point. Where the apparatus has replaceable screw elements and pin and/or paddle elements on the shafts, the skilled person will also readily be able, by routine testing, to identify an optimum configuration of such elements.

In one embodiment, the base component added to the reactor is ammonia which reacts with glyphosate acid to form the ammonium salt of glyphosate acid. The ammonia may be fed to the reactor as aqueous ammonia ($NH_4OH$), liquid anhydrous ammonia, gaseous anhydrous ammonia or combinations thereof through one or more input ports. Aqueous ammonia contributes additional water to the reactor thereby increasing the total amount of water fed to the reactor. Anhydrous ammonia, whether added in liquid or gaseous form, does not affect the total water balance. However, if fed in the liquid form, part or all of the liquid anhydrous ammonia may be converted to gaseous anhydrous ammonia upon entering the reaction vessel. The liquid anhydrous ammonia absorbs the heat of vaporization required to convert the liquid ammonia to gaseous ammonia from the reaction mass, thereby reducing the amount of heat that would otherwise need to be dissipated by other means, such as evaporation of water from the reaction mass or an external cooling system such as a cold water jacket. Accordingly, the ammonia is preferably fed to the reactor as anhydrous ammonia in the liquid form.

Whether the anhydrous ammonia is added in liquid form or gaseous form, at least some amount of gaseous anhydrous ammonia may subsequently exist in the reactor. Preferably, therefore, the reactor is designed to create and maintain a large interfacial area between the reaction mass and the internal atmosphere of the reactor vessel (i.e., the reactor mixes the reaction components such that a significant volume of gas is entrained in the reaction mass.) This interfacial area, herein referred to as the gas-paste interface, may affect the efficiency with which the glyphosate acid reacts with ammonia gas present in the internal atmosphere.

The apparatus described above (i.e, continuous single- or twin-shaft mixers/kneaders or solids processors) have been found particularly suitable when the base component used to neutralize the particulate glyphosate acid is anhydrous ammonia either in the gaseous or liquid state. When ammonia is injected at some distance from the input end of the vessel, the atmosphere within the chamber in the vicinity of the ammonia injection port becomes rich in ammonia, and the large gas-solid interface ensures rapid and efficient reaction of the ammonia with the glyphosate acid. Rapid consumption of the ammonia in the reaction leads to a rather steep declining concentration gradient of ammonia in the internal atmosphere of the chamber, towards both the input and the output end.

When the ammonia injection port is located at a suitable distance from each of the input and output ends, when the apparatus is operated at a suitable shaft rotation speed, and when the glyphosate acid and anhydrous ammonia are fed continuously at close to a stoichiometric ratio, the concentration of ammonia in the atmosphere at both ends of the chamber is normally so low that almost no ammonia is vented.

If the glyphosate acid is fed in the form of wet cake and no additional water, or only a small amount of additional water is required, the degree of mixing needed before contact with the ammonia is minimal. In this situation, the ammonia injection port can, if desired, be located close to the input end of the chamber. Back-leakage of ammonia gas from the input end can be substantially prevented by arranging that screw elements on the shafts draw wet cake uninterruptedly into the chamber so that no air continuum is permitted to form between the outside and inside of the chamber at the input end. Thus, in one embodiment: (i) glyphosate acid in the form of wet cake is pre-mixed with the dicarboxylate component and adjuvant and fed uninterruptedly by screw elements disposed in the aperture at the input end of the chamber in such a way that no air continuum forms that would permit back-leakage of ammonia at the input end; (ii) the shaft rotation speed is such that residence time of the reaction mass in the chamber is sufficient to permit substantial completion of the reaction forming the ammonium glyphosate salt; and, (iii) anhydrous ammonia is injected through a port located at a distance from the output end sufficient to result in substantially no venting of ammonia from the aperture at the output end. Even where the apparatus is designed for operation with close to zero emission of ammonia, it may be desirable to nevertheless treat the vented gases through a scrubber or equivalent device before release to the environment.

Particulate glyphosate acid may be added to the reactor either in dry powder, slurry or a wet cake form. Although not critical to the present invention, glyphosate acid particles having a nominal diameter in excess of about 400 µm or even about 300 µm may adversely affect the rate at which the reaction of particulate glyphosate acid with the base component occurs. In one embodiment, the particulate glyphosate acid may have a particle size distribution such that at least about 80% of the particles have a nominal diameter of less than about 400 µm in diameter and more preferably less than about 300 µm. In another embodiment, the glyphosate acid has a particle size distribution such that at least about 90% of the particles have a nominal diameter of less than about 400 µm in diameter and more preferably less than about 300 µm. In a particularly preferred embodiment, the particle size distribution is such that the median nominal diameter is from about 30 µm to about 230 µm, more preferably from about 50 µm to about 150 µm, and still more preferably from about 75 µm to about 125 µm. However, it should be noted that the particle size distribution may vary outside these ranges without departing from the scope of the present invention.

Preferably, the particulate glyphosate acid is added in the form of a wet cake having a moisture content of less than about 25%, typically from about 3% to about 18%, more typically from about 5% to about 15%, and in some embodiments from about 8% to about 15% or even from about 11% to about 13% by weight.

If the glyphosate acid is supplied in the form of wet cake, it may be necessary to feed the glyphosate acid to the neutralization reactor using a feeder, as described hereinafter, in order to maintain a constant feed rate. Glyphosate acid wet cake is a somewhat cohesive material that typically does not flow freely without the application of external force. Even when agitated, the wet cake tends to form "bridges" in static zones within the feed vessel where the wet cake is not in motion. Over time, these bridges can grow to the point that no wet cake flows from the feed vessel, resulting in an excess amount of base component in the downstream reaction step. When the reaction is carried out continuously, it is preferred that the glyphosate acid wet cake be fed to the reactor using equipment that reliably maintains a constant feed rate and that is not susceptible to bridging.

Figure 7:
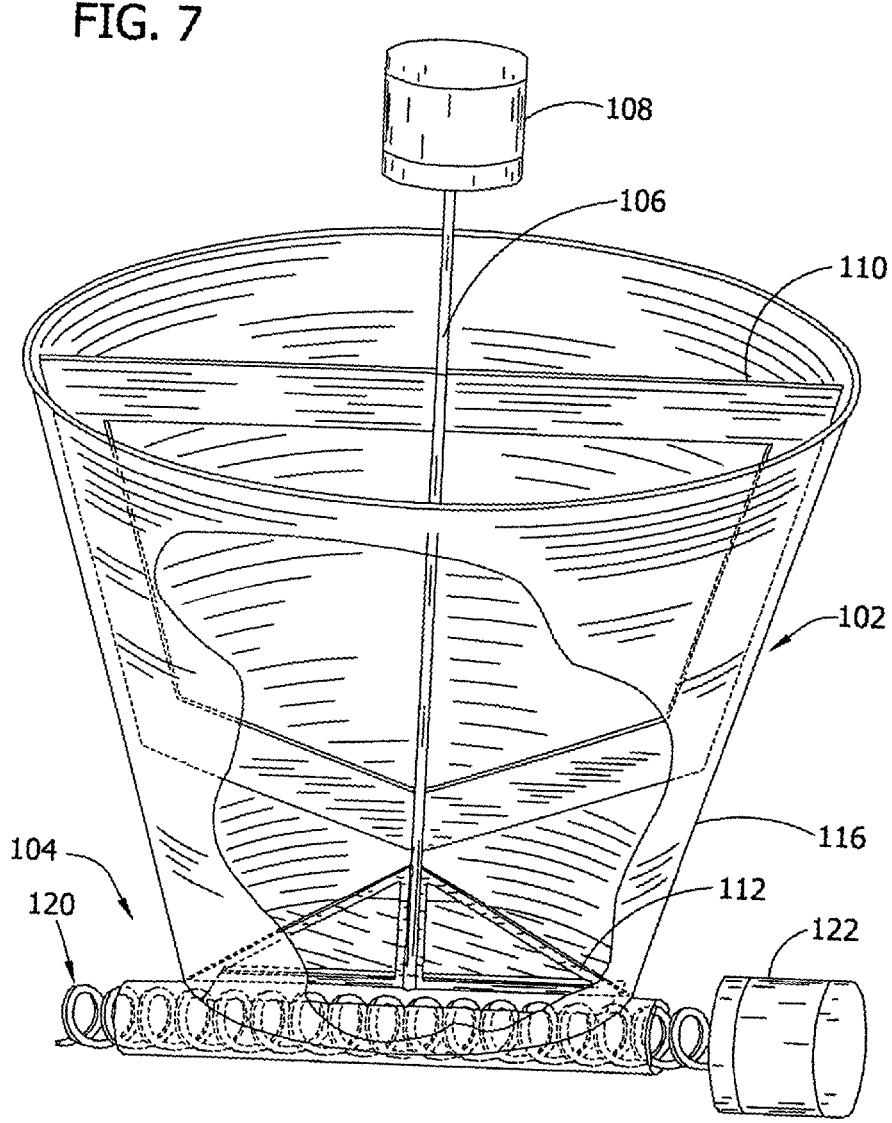
FIGS. 7 through 9 show a number of views of a gravimetric feeder suitable for supplying glyphosate acid wet cake at a constant feed rate in the process of the invention.

FIG. 7 depicts a suitable feeding apparatus that is designed to minimize the amount of bridging. The apparatus includes an upper feeder 102 and a lower feeder 104. The upper feeder includes a feed hopper 116 equipped with an agitator 106 driven by a motor 108.

The agitator includes upper blades 110 and lower blades 112. The upper blades are preferably open paddles shaped so as to fit closely within the walls of the hopper. Lower blades 112 are placed so as to maintain a minimum clearance, preferably less than about 1.6 mm from the top of the screw in the lower feeder so as to prevent accumulation of wet cake on the bottom plate. As shown more clearly in FIGS. 8 and 9, bottom plate 114 is formed with an integral trough 118 that forms the housing of lower feeder 104. Commercially available feeders that employ this type of agitator design typically provide about 6.5 mm clearance between the blade edges and the bottom plate. However, in the practice of the present invention, if the clearance between the blades and the bottom plate is this large, bridges of wet cake may form across the top of this trough, impeding or stopping the flow of wet cake to the lower feeder. Preferably, therefore, the clearance is less than about 6.5 mm, and more preferably less than about 1.6 mm, from the blade edge to the top of the screw to reduce the tendency of glyphosate wet cake to accumulate on the plate. It should be noted that the agitator speed may also affect the performance of the feeder. That is, if the agitator rotates too quickly, it may force material into the lower feed unit faster than the screw can transport the wet cake into the reactor. If the agitation speed is too low, the agitator will not break up the bridges forming in the hopper. The optimum agitator speed for a given feeder design may be readily determined by routine experimentation to ensure that the feed rate is not adversely affected and that the formation of bridges is sufficiently suppressed.

Figure 8:
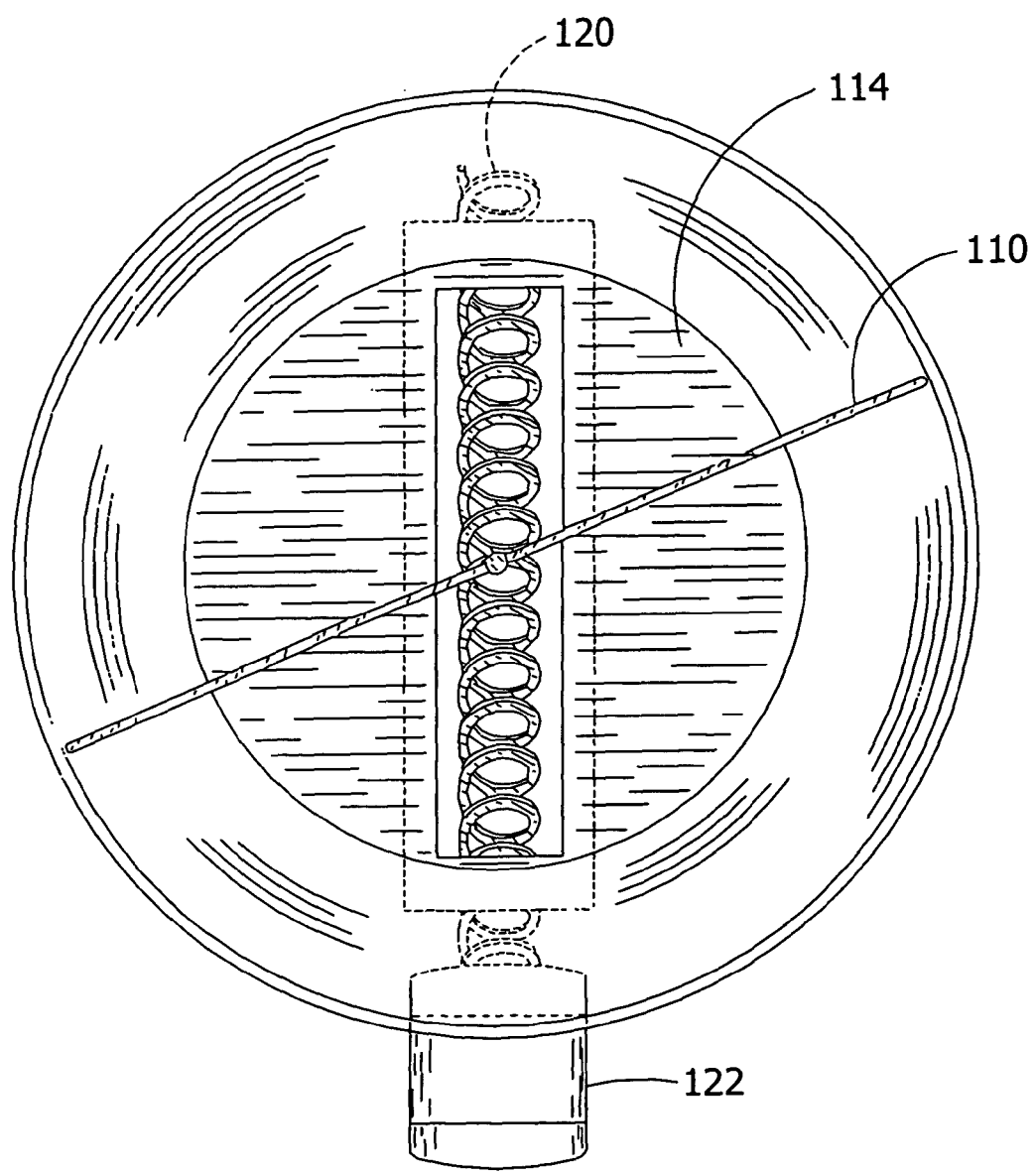
Figure 9:
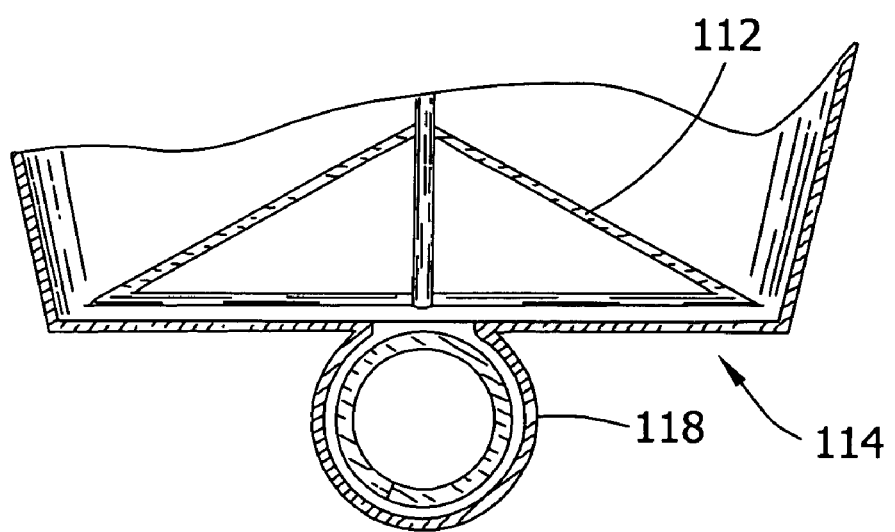

Lower feed unit 104 is preferably a conveyor capable of discharging material having a moisture content sufficient to cause bridging from the upper feeder 102 to the reactor. Preferably, the conveyor is a screw feeder comprising a single-helix, open-spiral auger 120 as shown in FIG. 8. While the glyphosate acid is preferably fed continuously to the process using equipment as described above, any equipment that reliably maintains a constant feed rate of moist glyphosate acid may be used without departing from the scope of the present invention. Such equipment is commercially available, for example, from Merrick Industries (Lynn Haven, Fla.).

In general, the amount of water fed to the reactor is preferably sufficient to contribute usefully to dissipation of heat by evaporative cooling. That is, the evaporation of water from the reaction mass dissipates some of the heat generated in the neutralization reaction. While the reaction may be carried out at temperatures as low as ambient temperatures, the temperature of the reaction mass typically increases rapidly due to the exothermic nature of the neutralization reaction. The temperature at which the reaction is carried out is typically from about 70° C. to about 105° C. and is more preferably about 100° C. Typically, the reaction mass is cooled to prevent overheating. The evaporation of water from the reaction mass reduces the amount of heat that would otherwise need to be removed by other means. As noted above, when the neutralization step is carried out in a solid state, the amount of water added is generally from about 2% to about 40% by weight, typically from about 2% to about 25% by weight of all of the components added to the reactor for the neutralization step. More typically, the total amount of water added to the reactor is from about 10% to about 25% and even more typically from about 13% to about 18% by weight of all of the glyphosate acid, base component, water, dicarboxylate component and adjuvant added to the reactor vessel. Within these ranges, the amount of water added to the reaction mass is not narrowly critical. In view of the considerations discussed above, the precise amount of water for a particular apparatus and set of reaction conditions may be readily determined by one of skill in the art. Generally the evaporation of water results in a decrease of about 1 to about 15, typically from about 1 to about 10 percentage points in the moisture content of the reaction mass during the neutralization step such that the neutralization reaction product discharged from the reactor may have a moisture content of from about 0.1% to about 20%. As noted above, the water may be added in combination with one or more of the other components (e.g., water in glyphosate acid wet cake). The portion or the water added with such other components may vary without departing from the scope of the present invention provided the total amount of water added is consistent with the above stated ranges. For example, where 100 parts by weight of glyphosate acid are mixed with 10 parts by weight of ammonia (both expressed on a water-free basis) and no other ingredients except water are added in the reaction step, a suitable amount of water is from about 12 to about 37 parts by weight, typically from about 14 to about 18.

Advantageously, the evaporation of water additionally reduces the amount of water that may need to be removed in a subsequent material processing step if a lower moisture content composition is desired. For example, the moisture content of the reaction mass may be reduced by evaporation of water to form a dry pesticidal powder mixture having a moisture content of less than about 2% by weight.

Figure 6:
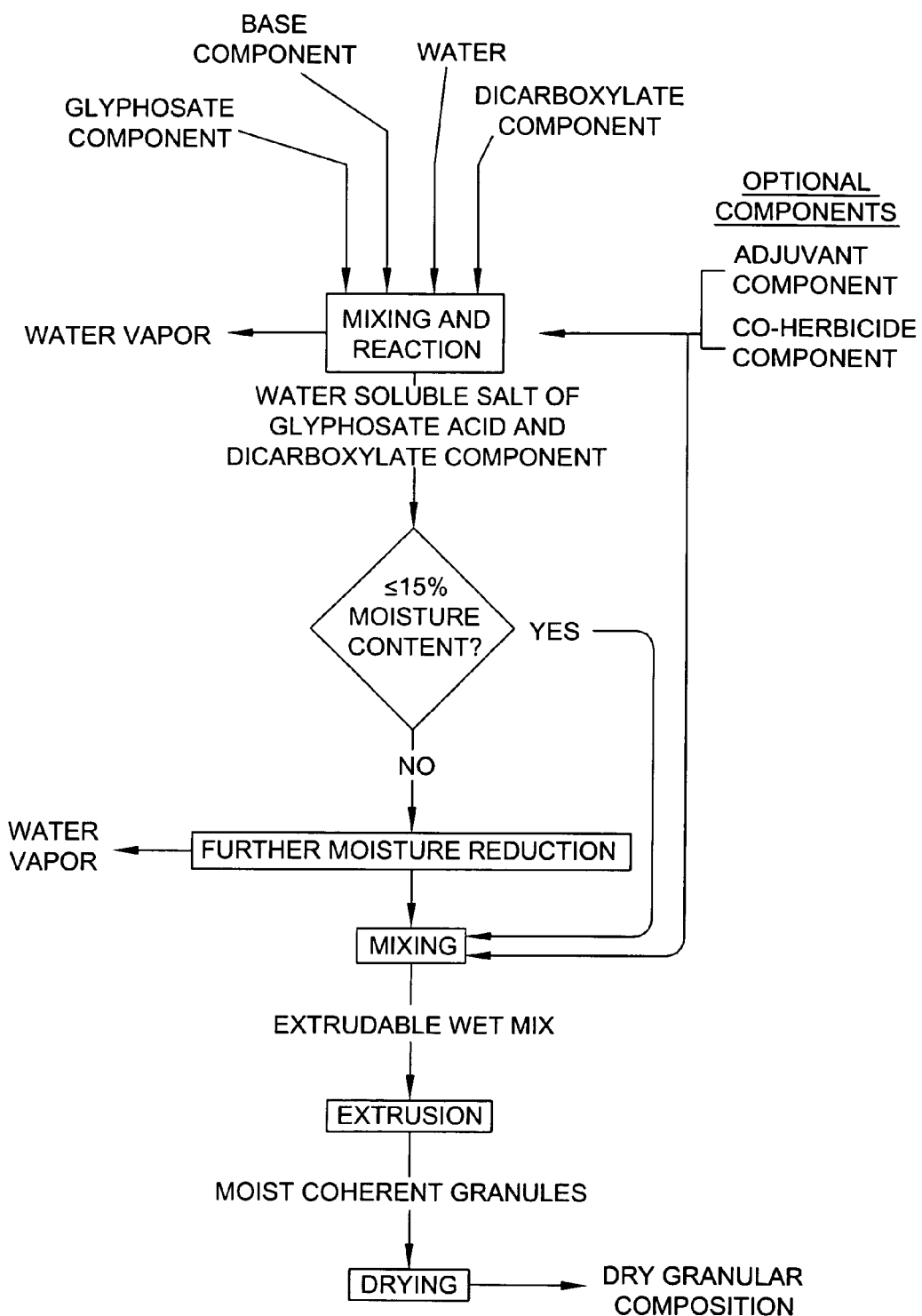
FIG. 6 shows a process flow diagram for combining a glyphosate component, a portion or all of which is glyphosate acid, a dicarboxylate component, a base component, water and optionally an adjuvant component and/or a co-herbicide component to form a water-soluble pesticidal paste composition and further processing the paste composition to form a dry granular pesticidal composition comprising a water-soluble salt of glyphosate acid and a dicarboxylate component.

In the embodiment shown in FIG. 6, the moisture content of the reaction mass is reduced to form a downstream processable paste comprising a water-soluble salt of glyphosate acid and a dicarboxylate component. Although some reduction in moisture content is desirable to form a suitable paste, it is also desirable to maintain a sufficient water concentration to sustain the homogeneity of the reaction mass to ensure the completion of the reaction. That is, the evaporation of some of the water in the reaction mass affects the flow characteristics of the reaction mass. Accordingly, the water is preferably fed to the reactor at a rate sufficient to provide not only the evaporative cooling effect as described above, but also to ensure the reaction mass may be readily homogenized with the degree of energy available in the mixing system used in the reactor, so that the acid-base reaction(s) proceed smoothly and completely producing a downstream processable paste. In some types of high-energy mixing or kneading equipment having an effective conductive cooling system in the form of, for example, a water jacket, a relatively stiff paste having relatively low moisture content is acceptable, whereas in lower-energy equipment or equipment having a less effective conductive cooling system it can be desirable to form a wetter, more fluid paste.

Typically, when a paste is desired, the moisture content of the neutralization reaction mass is reduced to from about 2% to about 20%, more typically from about 2% to about 18% by weight. Preferably, as indicated in FIG. 6, the moisture content of the reaction mass is reduced to no more than about 15% by weight, more preferably from about 2% to about 15%, even more preferably from about 2% to about 10%, still more preferably from about 2% to about 5% and especially from about 3% to about 5% by weight to form a pesticidal paste. It should be noted that a substantial amount of water may continue to evaporate from the reaction mass during cooling. Thus, the moisture content in the reaction mass is preferably determined after the composition has been allowed to cool to from about 50° C. to about 70° C. The moisture content can be measured using any means known in the art for determining such a composition. Devices capable of measuring the moisture content are commercially available, for example, from Denver Instrument Company (Arvada, Colo.). If the moisture content of the water-soluble glyphosate paste is greater than about 15% by weight, additional heat can be added to the reaction to increase water evaporation. Additionally or alternatively, further reduction in moisture content of the composition can be effected by application of heat and/or vacuum to the neutralization reaction product after completion of the neutralization reaction. Any moisture reduction or partial drying method known in the art can be used. To avoid the necessity for application of heat and/or vacuum to drive off further water, the process conditions are preferably such that the water-soluble glyphosate paste has a moisture content of no greater than about 15% by weight.

The water-soluble paste comprising a water-soluble salt of glyphosate acid and a dicarboxylate component produced by the process described in detail above can be packaged as a concentrate pesticidal composition, either as produced or dried, for example by drum drying to form solid flakes. In addition, depending on the amount of adjuvant added and the moisture content of the water-soluble glyphosate salt-containing paste, the paste may solidify upon cooling to form a mixture that "crumbles" to the touch.

The adjuvant component may be added in part or in whole to the reaction mass with the remaining adjuvant component being added downstream or may be added in its entirety downstream after completion of the neutralization reaction. The adjuvant component may be a single adjuvant or it may comprise two or more adjuvants. Where two or more adjuvants are added, they may be added separately to the reaction mass or they may first be blended together and the blend may then be added to the reaction mass. Other materials, including water and/or glycols, can optionally be admixed with the adjuvant component prior to addition to the reaction mass.

The adjuvant or adjuvant blend is preferably added in a liquid state. Solid adjuvant can be added in the solid state or alternatively can be heated to a temperature above its melting point and added in the liquid state. Solid adjuvants may also be added either as an aqueous slurry, or if the solubility of the adjuvant is sufficiently high, may be added as a solution. Liquid adjuvants may also be heated to improve the flow characteristics of the adjuvant.

The addition of an adjuvant to the reaction mass in solid state neutralization embodiments may increase the rate of formation of the water-soluble salt of glyphosate acid and reduce the flow resistance of the neutralization reaction mass or both, thereby providing a process having improved throughput.

When the neutralization step is carried out in a liquid state, the amount of water added to the reactor may be substantially higher than about 40% by weight of all the components combined in the reactor such that the reaction mass formed is an aqueous solution or slurry as described, for example, in U.S. Pat. No. 6,448,434 and U.S. Pat. No. 6,599,858, the entire disclosures of which are incorporated herein by reference. The liquid state neutralization of glyphosate acid may be suitably carried out as a batch, semi-batch or continuous reaction in one or more stirred tank reactors (STRs) and/or continuous stirred tank reactors (CSTRs). The stirred tank reactors may be operated in series or in parallel. The neutralization reaction product is a solution or slurry comprising a water-soluble salt of glyphosate acid and dicarboxylate component. The reaction product may then be subjected to material processing steps such as spray drying to form a powder, drying and pan granulation to form granules, or drum drying to form flakes. The dicarboxylate component and optionally one or more adjuvants may also be added as part of said spray drying, pan granulation and/or drum drying processes.

2. Neutralization of the Dicarboxylate Component

If the dicarboxylate component includes one or more dicarboxylic acids, the acid in the dicarboxylate component may be neutralized separately from the glyphosate component using any of the neutralization processes described above for neutralizing glyphosate acid. With reference to FIG. 4, dicarboxylic acid is combined with a base component such that the dicarboxylic acid is neutralized by the base component to form a salt of dicarboxylic acid. The salt of dicarboxylic acid may be combined with an adjuvant component to form a pesticide enhancer composition capable of enhancing the efficacy of glyphosate or may be combined with a water-soluble salt of glyphosate acid to form a dry pesticidal composition comprising a water-soluble salt of glyphosate, a dicarboxylate component and an adjuvant component.

In embodiments where a pesticide enhancer composition is produced, the adjuvant may be added to the dicarboxylate component before, during or after the neutralization of the dicarboxylic acid. Preferably, the adjuvant added to the dicarboxylate component to form the pesticide enhancer composition comprises a surfactant component and may optionally include a filler. The amounts of dicarboxylate component, surfactant component and optionally base component and/or filler combined to form the pesticide enhancer composition are determined such that the pesticide enhancer composition, when formed, has a concentration of dicarboxylate component which is generally from about 34% to about 90% by weight and typically from about 70% to about 90% by weight, has a concentration of surfactant which is generally from about 5% to about 50% by weight and typically from about 5% to about 20% by weight and has a concentration of filler, if any, which is generally no greater than about 34% by weight and typically from about 5% to about 10% by weight. The pesticide enhancer composition may be combined with a glyphosate component to form a water-soluble pesticidal composition or may be optionally subjected to further material processing and/or packaged separately as a pesticide enhancer composition.

While not necessary in the practice of the present invention, it may be desirable to prepare the pesticide enhancer composition such that the bulk density of the pesticide enhancer composition is roughly the same as the bulk density of a glyphosate component or a water-soluble pesticidal composition with the pesticide enhancer composition is to be subsequently combined. The filler is used to adjust the bulk density of the pesticide enhancer composition. That is, the type and amount of filler added may be varied to adjust the bulk density of the pesticide enhancer composition. By minimizing the difference in bulk density between the pesticide enhancer and the glyphosate component or water-soluble pesticidal composition, segregation of the materials is suppressed.

In another embodiment, a water-soluble salt of glyphosate acid is added to the dicarboxylate component mixture before, during or after the neutralization reaction occurs. Optionally, an adjuvant component, a co-herbicide component and/or water may also be added to the mixture before, during or after the neutralization reaction occurs. That is, the neutralization of dicarboxylic acid may be carried out separately or in the presence of the glyphosate component and/or the optional components discussed above.

Dicarboxylic acids may be extremely corrosive at elevated temperatures. For example, oxalic acid has been found to be extremely corrosive at temperatures of about 100° C. and may even be extremely corrosive at temperatures as low as about 75° C. Reactions in which dicarboxylic acids, such as oxalic acid, are neutralized with some base components, such as ammonia, ammonia hydroxide or sodium hydroxide may be highly exothermic. Such reactions may result in an increase in the temperature of the neutralization reaction mass and a corresponding increase in the corrosivity of the reaction mass. In embodiments where a portion or all of the dicarboxylate component is a dicarboxylic acid, the temperature of the dicarboxylic acid may be controlled to maintain the dicarboxylic acid below a temperature at which the corrosivity of the dicarboxylic acid becomes unacceptably high for the equipment surfaces which are in contact with the acid. Alternatively, the equipment may be designed such that surfaces exposed to the acid comprise a metal alloy resistant to such corrosivity such as AL6XN, Alloy 2205, Alloy 904L and Hastelloy C.

Surprisingly, in accordance with one embodiment of the present invention, it has been discovered that dicarboxylic acid may be neutralized in an endothermic reaction such that the temperature of the reaction mass does not increase to an unacceptably high temperature or even decreases during the reaction such that the corrosivity of the dicarboxylic acid is suppressed. Accordingly, in one embodiment, a dicarboxylic acid, such as oxalic acid, is neutralized with a base component that reacts endothermically with the dicarboxylic acid. Base components that react endothermically include, for example, sodium carbonate, sodium bicarbonate, ammonium carbonate, ammonium dicarbonate, trisodium phosphate or mixtures thereof. The endothermic neutralization has a cooling effect on the neutralization reaction mass thereby reducing the temperature and suppressing the corrosivity of the reaction mass.

3. Co-Neutralization of Glyphosate Acid and Dicarboxylic Acid

With reference to FIG. 5, dicarboxylic acid in the dicarboxylate component may be co-neutralized with glyphosate acid in the glyphosate component. The co-neutralization may be carried out in accordance with any of the neutralization embodiments described herein. The dicarboxylate component and the glyphosate component may be pre-blended prior to being added to the reactor or may be added concurrently to the neutralization reactor. As depicted in FIG. 5, a glyphosate component comprising particulate glyphosate acid, a dicarboxylate component comprising dicarboxylic acid, a base component, water and optionally, an adjuvant component and/or a co-herbicide are added to a reactor. At least a portion of the base component reacts with the glyphosate acid to form a water-soluble salt of glyphosate acid and/or with the dicarboxylic acid to form a salt thereof. In such an embodiment, the dicarboxylate component may be added to the reactor before or during the reaction of the glyphosate component and base component and may be pre-mixed with the glyphosate component prior to being added to the reactor.

Where dicarboxylic acid is co-neutralized with glyphosate acid by a base component, the relative proportions of the acids and base component added to the reactor, or in the case of a continuous reaction, the relative feed rates of the acids and base component added to the reactor may be varied to control the pH of the reaction mass to produce the desired salts based on the pKa of the acids. Typically, when a mixture of dicarboxylic acid and glyphosate acid is co-neutralized, the amount of base component added is approximately the stoichiometric amount required to neutralize at least a portion of the dicarboxylic acid and a substantial portion of the first proton of glyphosate acid such that the pH of the mixture is at least about 3, typically from about 3 to about 6 and more typically from about 3.5 to about 4.5. That is, at least about 50%, at least about 70%, at least about 80%, at least 90% or even 100% by weight or greater of the glyphosate acid is neutralized and all or any portion of the dicarboxylic acid present in the mixture is neutralized. As stated earlier, the amount of base component added may be varied to over or under neutralize the glyphosate and/or dicarboxylic acids present without departing from the scope of the present invention.

In one embodiment, glyphosate acid and oxalic acid are coneutralized in the reactor by anhydrous ammonia. Glyphosate acid is a tribasic acid with a pK1 of about 2.27, a pK2 of about 5.57 and a pK3 of about 10.25. Oxalic acid is a dibasic acid with a pK1 of about 1.25 and a pK2 of about 4.29. Typically, the degree of neutralization of the acids may be effected by controlling the amount of ammonia added and the final pH of the reaction product. Typically, the pH is controlled to a range of from about 3.5 to about 4.5 in the final reaction product. Under such reaction conditions, a substantial portion of the protons corresponding to the pK1 of both the oxalic acid and glyphosate acid would be replaced by ammonia cation. In addition, about 50% of the oxalic acid molecules will have the second proton corresponding to the pK2 of the oxalic acid replaced by ammonia cation, while the second and third protons from the glyphosate acid are left essentially intact, resulting in a mixture of mono-ammonium glyphosate, mono-ammonium and di-ammonium oxalate. Similarly, various mixtures of water-soluble glyphosate salts and oxalate salts may be formed by varying the amount of glyphosate acid, dicarboxylic acid and base component used as well as the pH of the mixture.

In another embodiment, the glyphosate acid may be over neutralized to a pH of up to about 5.5 in the reactor and subsequently mixed with a dicarboxylic acid such that at least a portion of the dicarboxylic acid is neutralized. For example, glyphosate acid may be over-neutralized with a base component supplying ammonium cations to form the di-ammonium glyphosate or mixtures of mono- and di-ammonium glyphosate. The di-ammonium glyphosate or mixtures of mono- and di-ammonium glyphosate may be subsequently mixed with a dicarboxylate component at least a portion of which is a dicarboxylic acid in a subsequent mixing step such as in a kneader. The mixture of the di-ammonium glyphosate or mixtures of mono- and di-ammonium glyphosate and dicarboxylic acid will tend to equilibrate such that the ammonium cation which replaced the second proton on the glyphosate acid will leave the glyphosate salt and replace a proton on the dicarboxylic acid such as the first proton on oxalic acid. In this manner, the ammonium glyphosate may be preferentially driven towards the mono-ammonium salt and the oxalic acid be partially or completely neutralized to form the mono-ammonium oxalate salt, di-ammonium oxalate salt or mixtures thereof to produce a mixture of the glyphosate salt and oxalate salt having the desired pH. Similarly, the dicarboxylate component may be over neutralized in the reactor and subsequently mixed with a glyphosate component, a portion or all of which is glyphosate acid. The pH to which the dicarboxylate component is over neutralized may be determined based on the amount of acid in the glyphosate component, the relative amounts of oxalate component and glyphosate component and the desired amount of neutralization of the glyphosate acid.

C. Down-Stream Processing

In another embodiment of the present invention, a mixture comprising water-soluble salts of glyphosate acid and a dicarboxylate component made in accordance with the process of the present invention (e.g., the neutralization reaction mixture in solution, slurry, paste or powder form or a dry mixture of the glyphosate and dicarboxylate components formed without neutralization) may be further processed to form a dry pesticidal composition (e.g, dry pesticidal granules, flakes or powder).

In one embodiment, additional adjuvant component may be added to the mixture of water-soluble salt of glyphosate acid and dicarboxylate component to form an extrudable wet mixture. The extrudable wet mixture is fed to an extruder having a screen through which the extrudable mixture is passed to form extrudate strands comprising the water-soluble salt of glyphosate acid and dicarboxylate component. Typically, the screens have apertures having a nominal diameter of from about 0.5 to about 3 mm, more typically from about 0.5 mm to about 2 mm, and in one embodiment from about 0.6 to about 1.5 mm. Screens with apertures having a nominal diameter within this range are commercially available, for example, from LCI Corporation (Charlotte, N.C.). The moist granules may be dried to further reduce the moisture concentration if desired. Any known drying method can be used, such as fluid bed drying. For example, a continuous fluid bed dryer may be used with continuous inward feed from the extruder and continuous outward feed, for example to a holding vessel or packaging unit, optionally via a classifying step as indicated below. The granules may be dried to a moisture content below about 1%, or even below about 0.5%, by weight. After drying, the granules can be packaged or held in a hopper or other storage vessel until ready for packaging, but it is generally preferred to first classify the granules, for example by sieving, to retain only those in a desired size range. An illustrative size range to be retained is larger than 40 mesh (about 0.6 mm) and smaller than 5 mesh (about 5 mm). Over- and under-sized granules or fragments or aggregates thereof can be recycled by adding them to the wet mix prior to extrusion.

The adjuvant component may be a surfactant component capable of enhancing the pesticidal efficacy of the finished product. In one embodiment, the surfactant component comprises one or more cationic surfactants. Depending upon the amount of adjuvant added to the reactor, one or more adjuvants (separately or as a blend, if more than one is used) may be combined with the neutralization reaction product (e.g. paste). The same adjuvant component added to the reaction mass may also be combined with the neutralization reaction product. Alternatively, the adjuvant component added to the reaction mass may differ in some respect (composition or relative proportion if more than one adjuvant) from the adjuvant component added to the neutralization reaction product. Typically, the amount of adjuvant added to the reaction mass will be less than the amount of adjuvant added to the neutralization reaction product.

The weight ratio of total adjuvant to glyphosate salt on a glyphosate acid equivalent basis depends, among other things, on the adjuvant component used. Such a ratio will often be a compromise between, on the one hand, providing sufficient adjuvant to give a high degree of pesticidal efficacy to the finished product, and on the other hand, less than the amount of adjuvant required to cause the finished granules become sticky or otherwise prone to aggregate and form lumps. The ratio of adjuvant to glyphosate salt which produces a high degree of pesticidal efficacy without producing a dry granular formulation having sticky granules may be determined as matter of routine testing by one of skill in the art. Taking into account both the adjuvant added to the reactor and the additional adjuvant added to the neutralization reaction product (e.g. paste), the weight ratio of total adjuvant to glyphosate salt (on an a.e. basis) in the finished granules is generally from about 1:9 to about 1:2, typically from about 1:6 to about 1:3 and where the adjuvant selected is a polyoxyethylene alkylamine, for example ethoxylated tallowamine, preferably from about 1:3 to about 1:5 on an a.e. basis.

The addition of adjuvant to the neutralization reaction product immediately on completion of the neutralization reaction step, without permitting the composition to cool, may result in the adjuvant failing to mix intimately with the neutralization product to form an extrudable mixture. Although some adjuvants are more tolerant than others in this respect, it is generally preferred to add the adjuvant component to the neutralization reaction product after the product has cooled to a temperature of from about 25° C. to about 75° C., more preferably about 50° C. to about 70° C. and more preferably about 70° C. In one embodiment of the present invention, the neutralization reaction product, adjuvant and dicarboxylate component are mixed to form an extrudable mixture in the same vessel in which the neutralization reaction step is carried out.

In another embodiment, reaction occurs in a continuous reactor as described above to form the neutralization reaction product which is then fed continuously to a separate mixing apparatus (e.g. a continuous kneader) wherein the additional adjuvant and optionally a dicarboxylate component is added to the neutralization product to form an extrudable mixture. Such continuous mixing apparatus are commercially available, for example, from Fuji Caudal Ltd. (Osaka, Japan) and Readco Manufacturing Inc. (York, Pa.).

In another embodiment, the mixture comprising water-soluble salts of glyphosate acid and a dicarboxylate component made in accordance with the process of the present invention is in a liquid form such as a slurry or solution (or water is added to the neutralization reaction product such that the mixture is in the form of a slurry or solution). An adjuvant component may be added to the mixture to form a solution or slurry comprising the water-soluble salt of glyphosate acid, dicarboxylate component and adjuvant. In one embodiment, the solution or slurry comprising the water-soluble salt of glyphosate acid, dicarboxylate component and adjuvant is spray dried to form a dry pesticidal powder composition. In another embodiment, the solution or slurry comprising the water-soluble salt of glyphosate acid, dicarboxylate component and adjuvant is pan granulated to form dry pesticidal granules. In yet another embodiment, the solution or slurry comprising the water-soluble salt of glyphosate acid, dicarboxylate component and adjuvant is contacted with a heated surface (e.g. a drum dryer) to form a solid deposit on the heated surface and scraped from the surface to produce a dry pesticidal flake composition.

EXAMPLES

The following Examples are provided for illustrative purposes only and are not intended to limit the scope of the present invention. The Examples will permit better understanding of the invention and perception of its advantages and certain variations of execution.

Example 1

Preparation of a Dry Pesticidal Composition by Mixing a Water-Soluble Salt of Glyphosate Acid and a Salt of Oxalic Acid Materials:
  Ammonium glyphosate as a dry powder with label purity of 87.5% glyphosate a.e.
  A nonionic surfactant (Huntsman L68-20)
  A liquid cationic surfactant (Sardonic T15)
  Di-ammonium oxalate (hereinafter DAO) monohydrate, milled into fine powder (ca. 200–400 mesh)
  Sodium sulfite
  Agnique DF 6889, a silicone anti-foam agent, as a 2% aqueous suspension.

Equipment:
  Raw materials were mixed on a laboratory scale Hobart mixer. Alternatively, a pilot or commercial scale kneader, such as a Fuji Caudal kneader, with a circulating water jacket capable of operating temperatures up to 100° C. may have been used.

Method:
  68.5 parts by weight of ammonium glyphosate, 15 parts by weight di-ammonium oxalate, and 0.4 parts by weight sodium sulfite were blended in the Hobart mixer for 1 to 3 minutes. The surfactants were then added, one at a time. The nonionic surfactant (Huntsman L68-20) was a solid at room temperature and was melted prior to addition. 8 parts by weight of nonionic surfactant (Huntsman L68-20) was poured into the mixer after the addition of 8 parts by weight of the liquid cationic surfactant (Sardonic T15). The composition was then mixed for 2 minutes with frequent scraping and stirring with a spatula or knife to break up any surfactant rich clumps. Finally, 5 mL of the anti-foam suspension was added to the mixer and the entire composition was worked into a sparsely wet dough. In this example, the water supplied by the 5 mL of the anti-foam suspension was sufficient to wet the dough adequately prior to extrusion.

Extrusion and Drying:

The thoroughly mixed dough was extruded through a screen with 1 mm die size. Extruded material was dried for 30 minutes in a dryer where the airflow temperature was 50° C. to yield the finished product in the form of dry granules 1 mm in diameter and approximately 2 to 4 mm in length. Approximately 100 parts by weight of dry pesticidal composition were obtained.

Subsequent analysis of this composition for glyphosate and oxalate was according to the specification. Assay results for glyphosate from multiple batches yielded the following results:

Target glyphosate a.e. 60.0%: DAO 15.0%
Batch 1: 60.2% glyphosate a.e.
Batch 2: 60.5% glyphosate a.e.
Batch 3: 60.1% glyphosate a.e.
Batch 4: 60.7% glyphosate a.e.

Example 2

Continuous Preparation of a Dry Pesticidal Composition by Addition of Over Neutralized Glyphosate Acid Salt to Oxalic Acid Dihydrate This example demonstrates a continuous process for the preparation of a dry pesticidal composition using glyphosate acid wet cake, oxalic acid dihydrate, liquid anhydrous ammonia, surfactant, and water.

An ammonium glyphosate mixture was prepared in a co-rotating twin-screw mixer/reactor with 2-inch diameter screws (manufactured by Readco, York, Pa.). Glyphosate acid wet cake containing approximately 12–13% by weight water was metered into the mixer at a rate of approximately 35 lb/hr. Liquid anhydrous ammonia was injected into the mixer at a rate of approximately 3.0 lb/hr, in slight stoichiometric excess with respect to the glyphosate acid. Surfactant was injected into the mixer at a rate of about 0.7 lb/hr. A small amount of water, 1 lb/hr, was injected into the mixer to attain a total moisture content of approximately 16% by weight of all of the components added to the mixture. The ammonia reacted with the glyphosate acid to produce an ammonium glyphosate paste. Water vapor was flashed from the paste product at the exit end of the mixer. The moisture content of the ammonium glyphosate paste was approximately 5% by weight. A 1% solution of paste in water had a pH range of 4.2 to 5.

The slightly over neutralized ammonium glyphosate paste was immediately transferred to a jacketed kneader, such as a Fuji Paudal. Water was circulated through the jacket at a temperature of from about 40° C. to about 80° C. For every 60 parts by weight of glyphosate acid, 11 parts by weight of oxalic acid dihydrate were metered into the kneader. Simultaneously, while being mixed in the kneader, 8 parts by weight of a polyoxyethylene alkylamine (Surfonic T15), 8 parts by weight of a molten alcohol ethoxylate (Huntsman L68-20), 5 parts by weight of water and 0.1 parts by weight of anti-foaming agent were added to the kneader. After addition, mixing was continued for about 10 minutes. The dough formed was then extruded, in a twin-screw extruder, such as a Fuji Paudal twin-screw extruder, fitted with screens having approximately 1 mm diameter apertures. The discrete, "spaghetti-like" extrudate strands were dried using a fluid bed drier, such as a Fitz-Aire fluid bed drier, and then sieved to remove any dust or large agglomerates. The finished product was in the form of dry granules about 1 mm in diameter and about 2 mm to 4 mm in length.

Table 1 shows the pH of the over-neutralized ammonium glyphosate paste prior to the addition of the oxalic acid dihydrate and the final pH of the formulation.

TABLE 1

| Formulation | Initial pH of the Over-Neutralized Paste | % Glyphosate a.e. | % Oxalate a.e. | Final pH of the Formulation |
|---|---|---|---|---|
| 1 | 4.5 | 68 | 5 | 3.4 |
| 2 | 4.75 | 68 | 5.2 | 3.5 |
| 3 | 4.9 | 68 | 5.2 | 3.9 |
| 4 | 4.9 | 60 | 9.9 | 3.3 |

Example 3

Batch Solid State Co-neutralization

Glyphosate acid and oxalic acid dihydrate may be neutralized simultaneously with ammonia to about pH 4. Surfactants may then be added to the neutralized reaction mass. In a reactor system comprised of a stainless steel ribbon, or other suitable blender, 79.53 parts by weight of standard grade glyphosate acid wet cake having an assayed moisture content of about 10% loss on drying (LOD) may be charged to the blender followed by the addition of 5.16 parts by weight of oxalic acid (anhydrous) and mixed therein. Once the first two ingredients are mixed, 0.2 parts by weight of sodium sulfite may also be charged to the blender and mixed. The reactor system may be equipped with a suitable hot air drying system such as an air-swept hammer mill supplied with hot air and an adapted dust collector, all of which are in communication with each other as by suitable connecting conduits. The mixture may be circulated within the hot air-swept mill system using an air inlet temperature of about 110° C. When the moisture content of the mixture is reduced to approximately 6% by weight, the air inlet temperature to the mill is reduced to about 80° C.

With the air temperature within the system being maintained at about 80° C., a solution of ammonium hydroxide (29% by weight ammonia) is then fed to the blender and sprayed by nozzles onto the mixture of acids to form a reaction mass. A total quantity of 27 parts by weight of liquid ammonium hydroxide may be introduced by spraying at a rate to ensure for progressive reduction of the total moisture content of the reaction mass. At the conclusion of the ammonium hydroxide addition, an additional 0.2 parts by weight of sodium sulfite are added.

The powdered reaction mass produced above may then be transferred to a jacketed kneader, such as a Fuji Caudal kneader, with water at a temperature of 80° C. circulating in the jacket. While being mixed in the kneader, 5.66 parts by weight of a polyoxyethylene alkylamine, 7.94 parts by weight of a molten alcohol ethoxylate, 5 parts by weight of water and 0.1 parts by weight of anti-foam agent are added to the kneader. After addition, mixing is continued for about 10 minutes. The dough that is formed is then extruded in a twin screw extruder, such as a Fuji Caudal twin-screw extruder, fitted with screens having approximately 1 mm diameter apertures. The discrete, "spaghetti-like" extrudate strands are dried using a fluid bed dryer such as a Fitz-Aire fluid bed drier and then sieved to remove any dust or large agglomerates.

Example 3B

Batch Slurry Neutralization for Preparing a Dry Pesticidal Composition in the Form of Flakes, Powder or Granules In a suitable water cooled, jacketed, agitated tank reactor, 50 parts by weight of water may be added and agitation started. Then 79.53 parts by weight of standard grade glyphosate acid wet cake having an assayed moisture content of about 10% LOD is charged to the tank followed by the addition of 7.22 parts by weight of oxalic acid dihydrate and intimately mixed. Once the first two ingredients are added to the water, 0.2 parts by weight of sodium sulfite is also charged to the tank whereupon it is intimately mixed. The tank vapor space is then inerted with nitrogen and 27 parts by weight of aqueous ammonia (29% by weight) is introduced below the surface of the liquid in the tank. The temperature of this material is maintained at about 50° C. and then fed to an atmospheric double drum drier such as the BUFLOVAK drier made by Blaw Knox Corporation. The drums are internally heated using superheated steam at 656 kPa to dry the mixture which is then scraped from the drums to form flakes. The flakes produced may then be ground in an air jet mill (such as a STURTEVANT MICRONIZER) to an average particle size of 10 microns or less.

In another experiment, the powder produced above is transferred to a jacketed kneader, such as a Fuji Caudal kneader, with water at a temperature of 80° C. circulating in the jacket. While being mixed in the kneader, 5.66 parts by weight of a polyoxyethylene alkylamine, 7.94 parts by weight of a molten alcohol ethoxylate, 5 parts by weight of water and 0.1 parts by weight of anti-foaming agent are added. After addition, mixing is continued for about 10 minutes. The dough that is formed is then extruded, for example in a Fuji Caudal twin-screw extruder, fitted with screens having approximately 1 mm diameter apertures to produce granular extrudate strands. The granular extrudate is dried using a fluid bed dryer, such as a Fitz-Aire fluid bed drier, and then sieved to remove any dust or large agglomerates.

Example 3C

Batch Slurry Neutralization for Preparing a Dry Pesticidal Composition in the Form of a Powder In a suitable water cooled, jacketed, agitated tank reactor, 50 parts by weight water are added and agitation started. Then 79.53 parts by weight of standard grade glyphosate acid wet cake having an assayed moisture content of about 10% LOD is charged to the tank followed by the addition of 5.16 parts by weight of oxalic acid (anhydrous) and intimately mixed. Once the first two ingredients are added to the water, 0.2 parts by weight of sodium sulfite is also charged to the tank whereupon it is intimately mixed. The tank vapor space is then inerted with nitrogen and 27 parts by weight of aqueous ammonia (29% by weight) is introduced below the surface of the liquid in the tank. The addition rate is adjusted such that the temperature of the mixture does not exceed about 80° C. This material is maintained at a temperature of at least about 50° C. While being mixed, 5.66 parts by weight of a polyoxyethylene alkylamine, 7.94 parts by weight of a molten alcohol ethoxylate and 0.1 parts by weight of anti-foaming agent are added. This heated mixture is then fed to a spray drier such as the NIRO drier (Niro Corp., Columbia, Md.) The powder product produced is sieved to remove any dust or large agglomerates.

Example 3D

Batch Slurry Neutralization for Preparing a Dry Pesticidal Composition in the Form of Flakes, Powder or Granules In a suitable water cooled, jacketed, agitated tank reactor, 50 parts by weight of water are added and agitation started. Then 79.53 parts by weight of standard grade glyphosate acid wet cake having an assayed moisture content of about 10% LOD is charged to the tank followed by the addition of 5.16 parts by weight of oxalic acid (anhydrous) and intimately mixed. Once the first two ingredients are added to the water, 0.2 parts by weight of sodium sulfite is also charged to the tank whereupon it is intimately mixed. The tank vapor space is then inerted with nitrogen and 27 parts by weight of aqueous ammonia (29% by weight) is introduced below the surface of the liquid in the tank. The temperature of this material is maintained at or above 50° C. and then fed to an atmospheric double drum drier, such as a BUFLOVAK drier made by Blaw Knox Corp. The drums are internally heated using superheated steam at 656 kPa to dry the product and the dried product is scraped from the drum dryer to form flakes. The flakes produced may then be ground in an air jet mill (STURTEVANT MICRONIZER) to an average particle size of 10 microns or less.

In another example, the above powder is slowly fed to a pan granulator such as a Koppers granulator (Sprout, Walden Corp., Muncy, Pa.) and a mixture of 5.66 parts by weight of a polyoxyethylene alkylamine, 7.94 parts by weight of a molten alcohol ethoxylate, 5 parts by weight of water and 0.1 parts by weight of anti-foaming agent are sprayed into the pan forming a pan granulated product which is then dried, such as for example in a Fitz-Aire fluid bed drier, and then sieved to remove any dust or large agglomerates.

Example 4

Continuous Solid State Co-neutralization for Preparing a Dry Pesticidal Composition This example demonstrates a continuous for the preparation of a dry pesticidal composition. Glyphosate acid wet cake, oxalic acid dihydrate, liquid anhydrous ammonia, water and surfactant are continuously fed to a mixer/reactor to form a paste composition. The paste was prepared in a co-rotating twin-screw mixer/reactor with 2-inch diameter screws (manufactured by Readco, York, Pa.). Chilled water was circulated through the mixer jacket. Glyphosate acid wet cake containing approximately 12–13% by weight moisture was metered into the mixer at a rate of approximately 35 lb/hr. Oxalic acid dihydrate was metered into the mixer in solid form at a rate of approximately 6.45 lbs./hr. The surfactant was injected into the mixer at a rate of approximately 0.7 lb./hr. Liquid anhydrous ammonia was injected into the mixer at a rate of approximately 4.23 lb/hr. Approximately 2 lb/hr of water was also injected into the reactor to attain a total moisture content of approximately 20% by weight of all components added to the mixer. The ammonia reacted with the glyphosate acid and oxalic acid dihydrate to produce the paste composition comprising ammonium glyphosate and ammonium oxalate. Water vapor was flashed from the product at the exit of the mixer. The moisture content of the paste was approximately 8–10% by weight. The pH of a 1% solution of the paste in water was approximately 4.

Approximately 7 parts by weight of surfactant was combined with approximately 35 parts by weight paste to form an extrudable mixture. The resulting mixture was extruded through a 0.8 mm die and dried in a fluid bed drier to produce dry water-soluble pesticidal granules containing ammonium glyphosate, ammonium oxalate and surfactant.

Example 5

Continuous Solid State Neutralization for Preparation of a Dry Pesticidal Composition This example demonstrates a continuous process for preparing a dry pesticidal composition. Glyphosate acid wet cake, di-ammonium oxalate, liquid anhydrous ammonia, water and surfactant are continuously fed to a mixer to form a paste composition. The paste may be prepared in a co-rotating twin-screw mixer/reactor with 2-inch diameter screws (manufactured by Readco, York, Pa.). Chilled water is circulated through the mixer jacket. Glyphosate acid wet cake containing approximately 12–13% by weight moisture is metered into the mixer at a rate of approximately 35 lb/hr. Di-ammonium oxalate is metered into the mixer at a rate of approximately 7.3 lb/hr. Surfactant is injected into the mixer at a rate of approximately 0.7 lb/hr. Liquid anhydrous ammonia is injected into the mixer at a rate of approximately 2.6 lb/hr. Water is injected into the mixer at a rate of 2 lb/hr to attain a total moisture content of approximately 20% by weight of all components added to the mixer. The ammonia reacts with the glyphosate acid to produce the ammonium glyphosate paste. Water vapor is flashed from the paste product at the exit of the mixer. The moisture content of the ammonium glyphosate/ammonium oxalate paste composition is approximately 8–10% by weight. The pH of a 1% solution of paste in water is approximately 4.5.

Approximately 7 parts by weight of surfactant is combined with approximately 35 parts by weight paste to form an extrudable mixture. The resulting mixture is extruded through a 0.8 mm die and dried in a fluid bed drier to produce dry water-soluble pesticidal granules containing ammonium glyphosate, di-ammonium oxalate and surfactant.

Example 5b

Continuous Solid State Neutralization for Preparation of a Dry Pesticidal Composition This example demonstrates a continuous process for preparing a dry pesticidal composition. Glyphosate acid wet cake, di-ammonium succinate, liquid anhydrous ammonia, water and surfactant are continuously fed to a mixer to form a paste composition. The paste may be prepared in a co-rotating twin-screw mixer/reactor with 2-inch diameter screws (manufactured by Readco, York, Pa.). Chilled water is circulated through the mixer jacket. Glyphosate acid wet cake containing approximately 12–13% by weight moisture is metered into the mixer at a rate of approximately 35 lb/hr. Di-ammonium succinate is metered into the mixer at a rate of approximately 7.3 lbs/hr. Surfactant is injected into the mixer at a rate of approximately 0.7 lb/hr. Liquid anhydrous ammonia is injected into the mixer at a rate of approximately 2.6 lb/hr. Water is also injected into the mixer at a rate of about 2 lb/hr, to attain a total moisture content of approximately 20% by weight of all components added to the mixer. The ammonia reacts with the glyphosate acid to produce an ammonium glyphosate paste. Water vapor is flashed from the product at the exit of the mixer. The moisture content of the ammonium glyphosate/ ammonium succinate paste is approximately 8–10% by weight. The pH of a 1% solution of the paste in water is approximately 4.5.

Approximately 7 parts by weight of surfactant is combined with approximately 35 parts by weight paste. The resulting mixture is extruded through a 0.8 mm die and dried in a fluid bed drier to produce dry water-soluble pesticidal granules containing ammonium glyphosate, di-ammonium, succinate and surfactant.

Example 6

Preparation of a Dry Pesticidal Composition Using Ammonium Glyphosate and Di-ammonium Oxalate Step 1—Preparation of ammonium glyphosate granules: In a kneader is combined 79 parts by weight of ammonium glyphosate (86.5% by weight a.e.) and 21 parts by weight of Sardonic T-15. Sufficient water is added to give a paste of consistency suitable for extrusion and the mixture is kneaded to the desired consistency. The resulting material is fed to a low pressure extruder or other suitable device and extruded as a granule with a diameter of approximately 1 mm. The resulting granule is dried to a constant moisture content in a fluid bed dryer.

Step 2—Preparation of di-ammonium oxalate enhancer granules: 40 parts by weight di-ammonium oxalate and 5 parts by weight of a filler, such as urea, were mixed in a kneader and 5 parts by weight of surfactant was added to the mixture and kneaded. Adequate amount of water (1 to 3 parts by weight) was added to make an extrudable dough. The resulting dough was fed to the extruder and the resulting granules were dried in a fluid bed drier. The bulk density of the DAO enhancer granules was matched with that of the ammonium glyphosate granules by altering the ratio of DAO and urea to the surfactant.

Step 3—Blending of ammonium glyphosate granules and di-ammonium oxalate enhancer granules: The resulting granules from the two processes were fed from the fluid bed dryers into a suitable mixer such as a batch mixer such as V-blender or double cone blender, or into a continuous mixer. The two granules were combined at the desired ratio for example, 100 parts by weight of the ammonium glyphosate granule can be combined with 20 parts by weight of the di-ammonium oxalate granule to give a ratio of 60 parts by weight of glyphosate acid to 13.3 parts by weight of di-ammonium oxalate monohydrate.

Example 7a

Continuous Solid State Co-neutralization Process for Preparation of a Dry Pesticidal Composition This example demonstrates a continuous process for preparation of a dry pesticidal composition. Glyphosate acid wet cake, oxalic acid dihydrate, liquid anhydrous ammonia, surfactant, and water are added to a mixer to form an ammonium glyphosate/ammonium oxalate paste composition. The paste was prepared in a co-rotating twin-screw mixer/reactor with 2-inch diameter screws (manufactured by Readco, York, Pa.). Approximately 35 lb/hr of glyphosate acid wet cake containing approximately 12–13% by weight moisture and 6.48 lb/hr of oxalic acid dihydrate were pre-blended and then metered into the mixer at a rate of approximately 41.48 lb/hr. The surfactant was injected into the mixer at a rate of approximately 0.7 lb./hr. Liquid anhydrous ammonia was injected into the mixer at a rate of approximately 4.14 lb/hr. Water was injected into the mixer at a rate of about 2 lb/hr to attain a total moisture content of approximately 20% by weight combining all components added to the mixer. The ammonia reacted with the glyphosate acid and oxalic acid dihydrate to produce an ammonium glyphosate/ammonium oxalate paste. Water vapor flashed from the paste product at the exit of the mixer. The moisture content of the resulting paste was approximately 8–10% by weight. The pH of a 1% solution of the resulting paste in water was approximately pH 4.

Approximately 7 parts by weight of surfactant was combined with approximately 35 parts by weight paste. The resulting mixture was extruded through a 0.8 mm die and dried in a fluid bed drier to produce a dry water-soluble pesticidal granules containing ammonium glyphosate, ammonium oxalate and surfactant.

Example 7b

Continuous Solid State Neutralization for Preparation of a Dry Pesticidal Composition This example demonstrates a continuous process for preparing a dry pesticidal composition. Glyphosate acid wet cake, di-ammonium oxalate, liquid anhydrous ammonia, surfactant, and water are continuously fed to a mixer to form a paste composition. The paste is prepared in a co-rotating twin-screw mixer/reactor with 2-inch diameter screws (manufactured by Readco, York, Pa.). Chilled water is circulated through the mixer jacket.

35 lb/hr of glyphosate acid wet cake containing approximately 12–13% by weight moisture and 7.3 lb/hr of di-ammonium oxalate are pre-blended and then metered into the mixer at a rate of approximately 42.3 lb/hr. The surfactant is injected into the mixer at a rate of approximately 0.7 lb/hr. Liquid anhydrous ammonia is injected into the mixer at a rate of approximately 2.6 lb/hr. Water is injected into the reactor at a rate of about 2 lb/hr to attain a total moisture content of approximately 20% by weight of all of the components added to the mixer. The ammonia reacts with the glyphosate acid to produce an ammonium glyphosate/di-ammonium oxalate paste. Water vapor is flashed from the paste product at the exit of the mixer. The moisture content of the ammonium glyphosate/di-ammonium oxalate paste is approximately 8–10% by weight. The pH of a 1% solution of the paste in water is approximately pH 4.5.

Approximately 7 parts by weight of surfactant is combined with approximately 35 parts by weight paste. The resulting mixture is extruded through a 0.8 mm die and dried in a fluid bed drier to produce a dry water-soluble pesticidal granules containing ammonium glyphosate, di-ammonium oxalate and surfactant.

Example 8

Downstream Processing of Water-Soluble Salts of Glyphosate Acid and Dicarboxylate Components to Form Granules, Flakes or Powders In this series of examples, the water-soluble glyphosate and oxalate salts can be prepared by any number of means, e.g. batch, dry blending, etc. This series focuses on combining the water-soluble glyphosate and oxalate salts with surfactants to produce a formulated product.

Example 8A

Pan Granulation

In a ribbon blender is combined 786 parts by weight of ammonium glyphosate (86.5% by weight a.e.), 80 parts by weight of di-ammonium oxalate, 929 parts by weight of atrazine, 20 parts by weight of sodium lignosulfonate (Reax 88B B MeadWestvaco Corp, Stamford, Conn.), 10 parts by weight of HiSil 233 (PPG Industries, Pittsburgh, Pa.), 40 parts by weight Montmorillonite Clay, and 40 by weight parts oxalic acid dihydrate. The material is blended until homogeneous. The resulting powder is slowly added to a 16-inch diameter pan granulator (Koppers Co., Inc., Muncy, Pa.). Sardonic T-15 (Huntsman Corp. Salt Lake City, Utah) is sprayed on the powder as the wheel turns. If granulation does not occur a small amount of water can be sprayed on the bed until an appropriate particle size is obtained. The amount needed will depend on the exact conditions and will be apparent to one skilled in the art. The resulting granules are recovered as the fall from pan and dried to constant moisture content. They are then screened using a Sweco screen (Sweco, Inc. Florence, Ky.) to obtain the desired range of mesh sizes. The over and under sized material is recycled into the process.

Example 8B

Flaking

In a ribbon blender is combined 786 parts by weight of ammonium glyphosate (86.5% by weight a.e.), 80 parts by weight of di-ammonium oxalate, 136 parts by weight of sodium dodecylbenzene sulfonate and 100 parts by weight of HiSil 233 (PPG Industries, Pittsburgh, Pa.). The resulting mixture is blended until homogeneous. The resulting powder is mixed with a small amount of water to achieve a suitable consistency for forming into tablets. The correct amount of water will depend on the properties and will be apparent to one skilled in the art. The resulting material is then formed into tablets in a tablet press (Carver, Inc. Wabash, Ind.). The resulting tablets are then ground to a coarse powder or small granule using a suitable dry mill such as a Fitz Commuting Mill (Fitzpatrick Company, Chicago, Ill.). The resulting material is then screened using a Sweco screen (Sweco, Inc. Florence, Ky.) to obtain the desired range of mesh sizes. The over and under sized material is recycled into the process.

Example 8C

Spray Drying

In a suitable tank equipped with an appropriate stirrer is combined 400 parts by weight of water and 200 parts by weight of Arquad T-50 (Tallowtrimethylammonium chloride (50%)(Akzo-Nobel, Arnhem, The Netherlands). In this solution are slurried 246 parts by weight of ammonium glyphosate (86.5% by weight a.e.) and 279 parts by weight of ammonium oxalate. The resulting slurry is sprayed into the chamber of a spray-drying tower at a temperature suitable for the evaporation of the water. The spray nozzle type and spraying pressure are adjusted to give the desired particle size. The resulting material is recovered using a cyclone collector. The resulting material is then screened using a Sweco screen (Sweco, Inc. Florence, Ky.) to obtain the desired range of mesh sizes. The over and under sized material is recycled into the process.

Example 9

Continuous Solid State Co-neutralization for Preparation of a Dry Pesticidal Composition This Example demonstrates a continuous process for the preparation of a dry pesticidal composition in which glyphosate acid and a dicarboxylic acid are co-neutralized. Particulate glyphosate acid, oxalic acid dihydrate, aqueous ammonia and water are mixed to form a paste containing ammonium glyphosate and ammonium oxalate. The paste is formed, mixed with a surfactant to form an extrudable paste composition and extruded in a continuous process in a single apparatus to form granules.

The apparatus to be used is a DNDG-62 twin-screw compounder/extruder with 62 mm co-rotating screws, manufactured by Buhler AG of Uzwil, Switzerland. Each of the screws, in addition to having screw elements of various lengths and pitches, was fitted coaxially with shearing and kneading elements. The screws were housed in a series of modular jacketed chamber sections known as barrels. For the present Example, the screws have a length/diameter ratio of 40 and are housed in a series of 9 barrels, numbered from the input end. Barrel 1 has an inlet for solid feed and barrels 2 and 8 have ports for liquid feed. Barrel 2 is chilled, barrels 3 and 4 are heated to approximately 130° C., barrels 5–7 are heated to approximately 150° C. and barrel 8 is heated to approximately 120° C. Barrels 1 and 9 are neither chilled nor heated. A vacuum of approximately –0.6 bar is applied to barrels 4 to 6 for removal of water vapor. Barrel 9 feeds directly to an extruder head. The screws were operated at 135 rpm, to give a production rate of extrudate of about 130 lb/h.

Glyphosate wet cake having about 13% by weight moisture content is fed to barrel 1 at a rate of approximately 90 lb/h. Oxalic acid dihydrate is fed into barrel 1 at the rate of approximately 10 lb/hr. Aqueous ammonia (about 30% by weight) is fed to barrel 2 at 36 lb/h. No additional water was added. The initial moisture content of the reaction mass is about 25% by weight.

Liquid surfactant is fed to barrel 8 at approximately 28 lb/h. The surfactant is a 4:1 by weight mixture of polyoxypropylene (8) ethoxytrimethylammonium chloride and polyoxyethylene (20) sorbitan lauryl ester. It is believed that reaction of the glyphosate acid and oxalic acid dihydrate with ammonia is substantially completed in barrel 2, with some reduction in moisture content of the resulting ammonium glyphosate paste. Thereafter, with application of heat to barrels 3–8 and vacuum to barrels 4–6, further reduction in moisture content of the paste occurs prior to extrusion. The finished product, upon dissolution in water to make a 1% glyphosate a.e. by weight solution, has a pH of 4.1.

Example 10

Preparation of a Neutralized Dicarboxylate-Containing Paste

To a 100 mL straight-walled glass vessel was added 42.6 g (112 mmol) of trisodium phosphate dodecahydrate (TSP). Oxalic acid dihydrate (18.9 g, 150 mmol) was added in aliquots to the dry TSP and mixed by manually stirring. The dry mixture soon took on a moist appearance and became progressively more damp with continued addition of the oxalic acid dihydrate and stirring. The final composition of the mixture was a flowable paste. The reaction of oxalic acid dihydrate and TSP was endothermic resulting in a temperature decrease from 24° C. to 14° C. The pH of a 1% solution of the sodium oxalate paste was 4.16. This material was formulated with glyphosate after drying to a powder, although it could be used in the paste form depending on the desired characteristics of the formulation.

Example 11

Preparation of a Neutralized Dicarboxylate-Containing Paste

Anhydrous trisodium phosphate (TSP) (24.6 g, 150 mmol) was added to a 50 mL straight-walled glass vessel. 1.8 g of water (100 mmol) was mixed in manually with an ensuing temperature rise from ambient to 56° C. Oxalic acid dihydrate (25.3 g, 200 mmol) was added in aliquots with manual stirring. When about one-half of the oxalic acid dihydrate was added, external heating was used to raise the temperature of the mixture. At an internal temperature of 70–75° C., an exothermic reaction ensued which increased the temperature to 108° C. The mixture was maintained at 70–80° C. during the remainder of the oxalic acid dihydrate addition to produce a stiff paste. This paste may be processed as is or cooled, dried, and ground to a powdery solid for use in formulations with a glyphosate component Example 12

Preparation of a Dicarboxylate-Containing Pesticide Enhancer Composition

A stainless steel planetary mixer of about 3 L capacity was pre-heated to 128° C. by circulating heated oil through the jacket of the mixer. To the pre-heated vessel was added 500 g of nonionic and cationic surfactant blend. To this was added 250 g (1.76 mol) of di-ammonium oxalate monohydrate and 37 g (0.29 mol) of oxalic acid dihydrate to simulate a partially neutralized mixture. The resultant slurry was heated to 91° C. The remaining charge of oxalic acid dihydrate (242 g, 1.92 mol) and ammonia (49 g, 2.88 mol) were added in seven aliquots that maintained an ammonia to oxalate molar ratio of 1.5. The slurry maintained a temperature of 99–100° C. during the hour long addition of the aliquots. While warm, the material could be poured from the reaction vessel, but at room temperature it took on the consistency of cookie dough. The pH of a 1% solution of this material was 4.25. Oxalic acid assay of the mixture was 36% by weight a.e, ammonia content was approximately 7% by weight and moisture content was 5.4% by weight, all within expectations. Analysis of the surfactant in the product showed no degradation or by-product formation. This material can be further formulated in its paste form.

In view of the above, it will be seen that the several objects of the invention are achieved. As various changes could be made in the above-described process without departing from the scope of the invention, it is intended that all matters contained in the above description be interpreted as illustrative and not in a limiting sense. In addition, when introducing elements of the present invention or the preferred embodiments thereof, the articles "a," "an," "the" and "said" are intended to mean that there are one or more of the elements. The terms "comprising," "including" and "having" are intended to be inclusive and mean that there may be additional elements other than the listed elements.

What is claimed is:

1. A process for preparing a water-soluble pesticidal composition comprising a water-soluble salt of glyphosate acid and a dicarboxylate component, the process comprising:
adding a glyphosate component comprising particulate glyphosate acid, a base component, water and optionally an adjuvant component to a reactor thereby causing a reaction of glyphosate acid and the base component to form a reaction mass comprising the water-soluble salt of glyphosate acid;
adding a dicarboxylate component to the reactor; and
reducing the moisture content of the reaction mass to form a water-soluble paste or dry water-soluble pesticidal composition comprising the water-soluble salt of glyphosate acid and the dicarboxylate component.

2. The process of claim 1 wherein the glyphosate component and at least a portion of the water are added to the reactor in the form of glyphosate acid wet cake.

3. The process of claim 2 wherein the dicarboxylate component is pre-mixed with the glyphosate acid wet cake prior to being added to the reactor.

4. The process of claim 1 wherein the base component is added to the reactor as a liquid.

5. The process of claim 1 wherein the base component is added to the reactor as a gas.

6. The process of claim 1 wherein the base component is selected from the group consisting of alkali metal hydroxides, alkaline earth metal hydroxides, carbonates of alkali metals, carbonates of alkaline earth metals, alkali metal phosphates, ammonium phosphates, ammonia, ammonium carbonate, ammonium bicarbonate, ammonium hydroxide and mixtures thereof.

7. The process of claim 6 wherein the base component is selected from the group consisting of sodium hydroxide, potassium hydroxide, magnesium hydroxide, calcium hydroxide, sodium carbonate, sodium bicarbonate, sodium phosphate, disodium phosphate, trisodium phosphate, potassium phosphate, ammonium phosphates, ammonia, ammonium carbonate, ammonium bicarbonate, ammonium hydroxide and mixtures thereof.

8. The process of claim 7 wherein the base component is ammonia such that the water-soluble salt of glyphosate acid in the reaction mass is ammonium glyphosate.

9. The process of claim 7 wherein the base component is potassium hydroxide such that the water-soluble salt of glyphosate acid in the reaction mass is potassium glyphosate.

10. The process of claim 7 wherein the base component is sodium hydroxide such that the water-soluble salt of glyphosate acid in the reaction mass is sodium glyphosate.

11. The process of claim 1 wherein the molar ratio of the base component to glyphosate acid added to the reactor is from about 0.8 to about 1.25.

12. The process of claim 11 wherein the molar ratio of the base component to glyphosate acid added to the reactor is from about 0.9 to about 1.1.

13. The process of claim 11 wherein the molar ratio of the base component to glyphosate acid added to the reactor is from about 0.95 to about 1.05.

14. The process of claim 1 wherein the dicarboxylate component added to the reactor is selected from the group consisting of dicarboxylic acids, salts of dicarboxylic acids, anhydrides of dicarboxylic acids, esters of dicarboxylic acids, amides of dicarboxylic acids, halides of dicarboxylic acids, precursors of dicarboxylic acids and mixtures thereof.

15. The process of claim 14 wherein the dicarboxylate component added to the reactor comprises a salt of a dicarboxylic acid.

16. The process of claim 14 wherein the dicarboxylate component added to the reactor comprises a salt of a dicarboxylic acid selected from the group consisting of alkali metal salts of dicarboxylic acids, alkanolamine salts of dicarboxylic acids, alkylamine salts of dicarboxylic acids and mixtures thereof.

17. The process of claim 14 wherein the dicarboxylate component added to the reactor comprises a salt of a dicarboxylic acid selected from the group consisting of sodium salts of dicarboxylic acids, potassium salts of dicarboxylic acids, isopropylamine salts of dicarboxylic acids and mixtures thereof.

18. The process of claim 14 wherein the dicarboxylate component added to the reactor comprises a dicarboxylic acid, the dicarboxylic acid reacting with the base component to form a salt of the dicarboxylic acid in the reaction mass, the dicarboxylate component of the pesticidal composition comprising the salt of the dicarboxylic acid formed in the reaction mass.

19. The process of claim 18 wherein the dicarboxylate component added to the reactor comprises a dicarboxylic acid selected from the group consisting of oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, terephthalic acid and mixtures thereof.

20. The process of claim 19 wherein the dicarboxylate component added to the reactor comprises oxalic acid.

21. The process of claim 14 wherein the dicarboxylate component added to the reactor is selected from the group consisting of salts of oxalic acid, esters of oxalic acid and mixtures thereof.

22. The process of claim 14 wherein the dicarboxylate component added to the reactor comprises a salt of oxalic acid selected from the group consisting of alkali metal salts of oxalic acid, ammonium salts of oxalic acid, alkanolamine salts of oxalic acid, alkylamine salts of oxalic acid and mixtures thereof.

23. The process of claim 14 wherein the dicarboxylate component added to the reactor comprises a salt of oxalic acid selected from the group consisting of potassium oxalate, di-potassium oxalate, sodium oxalate, di-sodium oxalate, ammonium oxalate, di-ammonium oxalate, diethanolamine oxalate, dimethylamine oxalate and mixtures thereof.

24. The process of claim 1 wherein an adjuvant component is added to the reactor.

25. The process of claim 24 wherein the adjuvant component added to the reactor is selected from the group consisting of a surfactant component, anti-foaming agent, filler, humectant, symptomatology agent, desiccant, lubricant, scavenger and mixtures thereof.

26. The process of claim 25 wherein the adjuvant component added to the reactor comprises a surfactant component selected from the group consisting of nonionic surfactants, cationic surfactants, anionic surfactants, amphoteric surfactants, silicone surfactants, fluorocarbon surfactants and mixtures thereof.

27. The process of claim 26 wherein the surfactant component added to the reactor comprises a cationic surfactant.

28. The process of claim 26 wherein the surfactant component added to the reactor comprises an amphoteric surfactant.

29. The process of claim 26 wherein the surfactant component added to the reactor comprises a nonionic surfactant.

30. The process of claim 29 wherein the surfactant component added to the reactor comprises is selected from the group consisting of alkyl polyglycosides (APGs), polyoxyethylene $C_{16-22}$ alkylethers and mixtures thereof.

31. The process of claim 1 wherein the total amount of water added to the reactor is at least about 2% by weight of all of the glyphosate component, dicarboxylate component, base component, water and adjuvant component added to the reactor.

32. The process of claim 31 wherein the total amount of water added to the reactor is from about 2% to about 40% by weight of all of the glyphosate component, dicarboxylate component, base component, water and adjuvant component added to the reactor.

33. The process of claim 32 wherein the total amount of water added to the reactor is from about 2% to about 25% by weight of all of the glyphosate component, dicarboxylate component, base component, water and adjuvant component added to the reactor.

34. The process of claim 1 wherein the reaction between the particulate glyphosate acid and the base component generates heat causing partial evaporation of the water from the reaction mass.

35. The process of claim 34 wherein the temperature of the reaction mass is from about 70° C. to about 105° C.

36. The process of claim 34 wherein the moisture content of the reaction mass is reduced to form a paste containing the water-soluble salt of glyphosate acid, the paste having a moisture content of from about 2% to about 20% by weight.

37. The process of claim 36 wherein the paste formed has a moisture content of from about 2% to about 18% by weight.

38. The process of claim 36 wherein the paste formed has a moisture content of from about 2% to about 15% by weight.

39. The process of claim 36 wherein the paste formed has a moisture content of from about 2% to about 10% by weight.

40. The process of claim 36 wherein the paste formed has a moisture content of from about 2% to about 5% by weight.

41. The process of claim 36 wherein the paste formed has a moisture content of from about 3% to about 5% by weight.

42. The process of claim 36 wherein the pH of the paste formed is from about 3 to about 6.

43. The process of claim 36 wherein the pH of the paste formed is from about 3.5 to about 4.5.

44. The process of claim 36 further comprising discharging the paste from the reactor, the paste discharged from the reactor comprising the water-soluble salt of glyphosate acid and the dicarboxylate component.

45. The process of claim 44 wherein additional dicarboxylate component is added to the paste discharged from the reactor.

46. The process of claim 44 wherein an adjuvant component is added to the paste discharged from the reactor.

47. The process of claim 46 wherein the adjuvant component added to the paste discharged from the reactor is selected from the group consisting a surfactant component, anti-foaming agent, filler, humectant, symptomatology agent, desiccant, lubricant, scavenger and mixtures thereof.

48. The process of claim 46 wherein the adjuvant component added to the paste discharged from the reactor is a surfactant component, the paste discharged from the reactor and the surfactant component forming an extrudable paste mixture, the surfactant component selected from the group consisting of nonionic surfactants, cationic surfactants, anionic surfactants, amphoteric surfactants, silicone surfactants, fluorocarbon surfactants and mixtures thereof.

49. The process of claim 48 wherein the surfactant component added to the paste discharged from the reactor comprises a cationic surfactant.

50. The process of claim 48 wherein the surfactant component added to the paste discharged from the reactor comprises an amphoteric surfactant.

51. The process of claim 48 wherein the surfactant component added to the paste discharged from the reactor comprises a nonionic surfactant.

52. The process of claim 51 wherein the surfactant component added to the paste discharged from the reactor comprises is selected from the group consisting of alkyl polyglycosides (APGs), polyoxyethylene $C_{16-22}$ alkylethers and mixtures thereof.

53. The process of claim 48 further comprising feeding the extrudable paste mixture comprising the paste discharged from the reactor and the surfactant component to an extruder having a screen through which the extrudable paste mixture is extruded to form the water-soluble pesticidal composition in the form of extrudate strands comprising the water-soluble salt of glyphosate acid and the dicarboxylate component.

54. The process of claim 48 wherein an adjuvant component is added to the reactor.

55. The process of claim 48 wherein the adjuvant component is added to the reactor and/or to the paste discharged from the reactor in an amount such that the weight ratio of total adjuvant to the water-soluble salt of glyphosate is from about 1:20 to about 1:2 on an acid equivalent basis.

56. The process of claim 31 wherein the total amount of water added to the reactor is at least about 40% by weight of all of the glyphosate component, dicarboxylate component, base component, water and adjuvant component added to the reactor and the reaction mass formed is a slurry or solution comprising the water-soluble salt of glyphosate acid and the dicarboxylate component.

57. The process of claim 56 wherein the reaction mass further comprises an adjuvant component.

58. The process of claim 56 further comprising reducing the moisture content of the reaction mass to less than about 2% by weight to form a dry water-soluble pesticidal composition comprising the water-soluble salt of glyphosate acid and the dicarboxylate component.

59. The process of claim 58 further comprising pan granulating the reaction mass to form a dry granular pesticidal composition.

60. The process of claim 58 further comprising spray drying the reaction mass to form a dry particulate pesticidal composition.

61. The process of claim 58 further comprising:
drying the reaction mass by contacting the reaction mass with a heated surface to form a solid deposit on the heated surface; and
scraping the solid deposit off the heated surface to produce a dry pesticidal flake composition.

62. A process for preparing a water-soluble pesticidal composition comprising a water-soluble salt of glyphosate acid and a dicarboxylate component, the process comprising:
  adding a glyphosate component comprising particulate glyphosate acid, a base component, water and optionally an adjuvant component to a reactor thereby causing a reaction of glyphosate acid and the base component to form a reaction mass comprising the water-soluble salt of glyphosate acid;
  reducing the moisture content of the reaction mass using the heat generated by the reaction between the particulate glyphosate acid and the base component to cause partial evaporation of the water from the reaction mass and form a paste containing the water-soluble salt of glyphosate acid, the paste having a moisture content of from about 2% to about 20% by weight; and
  adding a dicarboxylate component to the reaction mass and/or to the paste.

63. A process for preparing a dry water-soluble pesticidal composition comprising one or more water-soluble salts of glyphosate acid and a dicarboxylate component, the process comprising mixing a glyphosate component comprising one or more water-soluble salts of glyphosate acid present in a paste and a dicarboxylate component to form a dry pesticidal composition comprising one or more water-soluble salts of glyphosate acid and the dicarboxylate component wherein the glyphosate component optionally contains sources of glyphosate other than the water-soluble salts of glyphosate acid provided that at least about 50% by weight a.e. of the glyphosate component is one or more water-soluble salts of glyphosate acid.

64. The process of claim 63 wherein at least about 75% by weight a.e. of the glyphosate component is one or more water-soluble salts of glyphosate acid.

65. The process of claim 63 wherein at least about 90% by weight a.e. of the glyphosate component is one or more water-soluble salts of glyphosate acid.

66. The process of claim 63 wherein the glyphosate component consists essentially of one or more water-soluble salts of glyphosate acid.

67. The process of claim 65 wherein the glyphosate component comprises one or more water-soluble salts of glyphosate acid selected from the group consisting of ammonium salts of glyphosate acid, alkali metal salts of glyphosate acid, alkaline earth metal salts of glyphosate acid and alkylamine salts of glyphosate acid.

68. The process of claim 67 wherein the glyphosate component comprises one or more water-soluble salts of glyphosate acid selected from the group consisting of ammonium salts of glyphosate acid, sodium salts of glyphosate acid, potassium salts of glyphosate acid and isopropylamine salts of glyphosate acid.

69. The process of claim 67 wherein the dicarboxylate component is selected from the group consisting of dicarboxylic acids, salts of dicarboxylic acids, anhydrides of dicarboxylic acids, esters of dicarboxylic acids, amides of dicarboxylic acids, halides of dicarboxylic acids, precursors of dicarboxylic acids and mixtures thereof.

70. The process of claim 69 wherein the dicarboxylate component comprises a salt of a dicarboxylic acid.

71. The process of claim 69 wherein the dicarboxylate component comprises a salt of a dicarboxylic acid selected from the group consisting of alkali metal salts of dicarboxylic acids, alkanolamine salts of dicarboxylic acids, alkylamine salts of dicarboxylic acids and mixtures thereof.

72. The process of claim 69 wherein the dicarboxylate component comprises a salt of a dicarboxylic acid selected from the group consisting of sodium salts of dicarboxylic acids, potassium salts of dicarboxylic acids, isopropylamine salts of dicarboxylic acids and mixtures thereof.

73. The process of claim 69 wherein the dicarboxylate component comprises a dicarboxylic acid.

74. The process of claim 69 wherein the dicarboxylate component comprises a dicarboxylic acid selected from the group consisting of oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, terephthalic acid and mixtures thereof.

75. The process of claim 69 wherein the dicarboxylate component comprises oxalic acid.

76. The process of claim 69 wherein the dicarboxylate component is selected from the group consisting of salts of oxalic acid, esters of oxalic acid and mixtures thereof.

77. The process of claim 69 wherein the dicarboxylate component comprises a salt of oxalic acid selected from the group consisting of alkali metal salts of oxalic acid, ammonium salts of oxalic acid, alkanolamine salts of oxalic acid, alkylamine salts of oxalic acid and mixtures thereof.

78. The process of claim 69 wherein the dicarboxylate component comprises a salt of oxalic acid selected from the group consisting of potassium oxalate, di-potassium oxalate, sodium oxalate, di-sodium oxalate, ammonium oxalate, di-ammonium oxalate, diethanolamine oxalate, dimethylamine oxalate and mixtures thereof.

79. The process of claim 69 further comprising mixing an adjuvant component with the glyphosate component and the dicarboxylate component such that the dry pesticidal composition comprises one or more water-soluble salts of glyphosate acid, the dicarboxylate component and the adjuvant component.

80. The process of claim 79 wherein the adjuvant component comprises a surfactant component, the surfactant component selected from the group consisting of nonionic surfactants, cationic surfactants, anionic surfactants, amphoteric surfactants, silicone surfactants, fluorocarbon surfactants and mixtures thereof.

81. The process of claim 80 wherein the concentration of the adjuvant component in the dry pesticidal composition is from about 5% to about 50% by weight.

82. The process of claim 80 wherein the concentration of the adjuvant component in the dry pesticidal composition is from about 5% to about 25% by weight.

83. The process of claim 80 wherein the weight ratio of adjuvant component to the glyphosate component is at least about 1:500.

84. The process of claim 80 wherein the weight ratio of adjuvant component to glyphosate component is from about 1:20 to about 1:2.

85. The process of claim 69 further comprising mixing an adjuvant component and optionally water with the glyphosate component and the dicarboxylate component to form an extrudable mixture comprising the glyphosate component, the dicarboxylate component, the adjuvant component and optionally water and extruding the extrudable mixture to form the dry pesticidal composition in the form of granules.

86. A process for preparing a pesticide enhancer composition comprising a salt of a dicarboxylic acid and a surfactant component, the process comprising:

combining a dicarboxylate component comprising the dicarboxylic acid, a base component and a surfactant component in a reactor thereby causing the reaction between the dicarboxylic acid and the base component and forming the enhancer composition as a paste or dry pesticidal enhancer composition comprising the salt of the dicarboxylic acid and the surfactant component.

87. The process of claim 86 wherein the dicarboxylate component comprises a dicarboxylic acid selected from the group consisting of oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, terephthalic acid and mixtures thereof.

88. The process of claim 86 wherein the dicarboxylate component comprises oxalic acid.

89. The process of claim 86 further comprising adding a filler component to the reactor.

90. The process of claim 86 wherein the concentration of the salt of the dicarboxylic acid in the enhancer composition is from about 34% to about 90% by weight a.e.

91. The process of claim 90 wherein the concentration of the surfactant in the enhancer composition is from about 5% to about 50% by weight.

92. The process of claim 90 further comprising adding a filler component to the reactor.

93. The process of claim 92 wherein the concentration of the filler in the enhancer composition is no greater than about 34% by weight.

94. The process of claim 93 wherein the concentration of the filler in the enhancer composition is from about 5% to about 10% by weight.

95. The process of claim 86 wherein the concentration of the salt of the dicarboxylic acid in the enhancer composition is from about 70% to about 90% by weight a.e.

96. The process of claim 95 wherein the concentration of the surfactant in the enhancer composition is from about 5% to about 50% by weight.

97. The process of claim 95 wherein the concentration of the surfactant in the enhancer composition is from about 5% to about 20% by weight.

98. The process of claim 97 further comprising adding a filler component to the reactor.

99. The process of claim 98 wherein the concentration of filler in the enhancer composition is from about 5% to about 10% by weight.

\* \* \* \* \*